US012668795B2

(12) United States Patent (10) Patent No.: US 12,668,795 B2
Corti et al. (45) Date of Patent: Jun. 30, 2026

(54) INHIBITOR OF miR-129 AND USES THEREOF

(71) Applicants: UNIVERSITÀ DEGLI STUDI DI MILANO BICOCCA, Milan (IT); FONDAZIONE IRCCS "CA' GRANDA—OSPEDALE MAGGIORE" POLICLINICO, Milan (IT)

(72) Inventors: Stefania Corti, Milan (IT); Silvia Maria Luisa Barabino, Milan (IT); Monica Nizzardo, Milan (IT); Alessia Loffreda, Milan (IT)

(73) Assignee: FONDAZIONE IRCCS "CA' GRANDA—OSPEDALE MAGGIORE" POLICLINICO DI MILANO, Milan (IT)

( * ) Notice: Subject to any disclaimer, the term of this patent is extended or adjusted under 35 U.S.C. 154(b) by 1191 days.

(21) Appl. No.: 17/598,627

(22) PCT Filed: Mar. 26, 2020

(86) PCT No.: PCT/EP2020/058571
§ 371 (c)(1),
(2) Date: Sep. 27, 2021

(87) PCT Pub. No.: WO2020/193709
PCT Pub. Date: Oct. 1, 2020

(65) Prior Publication Data
US 2022/0162611 A1 May 26, 2022

(30) Foreign Application Priority Data
Mar. 27, 2019 (IT) ........................ 102019000004571

(51) Int. Cl.
*C12N 15/113* (2010.01)
*C12Q 1/6883* (2018.01)

(52) U.S. Cl.
CPC .......... *C12N 15/113* (2013.01); *C12Q 1/6883* (2013.01); *C12N 2310/113* (2013.01); *C12N 2310/3233* (2013.01); *C12Q 2600/178* (2013.01)

(58) Field of Classification Search
CPC ............ C12N 15/113; C12N 2310/113; C12N 2310/3233; C12Q 1/6883; C12Q 2600/178
See application file for complete search history.

(56) References Cited

FOREIGN PATENT DOCUMENTS

KR         20130083964 A         7/2013

OTHER PUBLICATIONS

Wen et al. "Small Molecules Targeting MicroRNA for Cancer Therapy: Promises and Obstacles". J Control Release. Aug. 6, 2015; 219:237-247. doi: 10.1016/j.jconrel.2015.08.011 (Year: 2015).*
Myers et al. "Overview of Transgenic Mouse Models for Alzheimer's Disease". Current Protocols in Neuroscience, 89, e81, 2019. doi: 10.1002/cpns.81 (Year: 2019).*
Benatar et al. "Defining pre-symptomatic amotrophic lateral sclerosis". Amyotroph Lateral Scler Frontotemporal Degener. Aug. 2019 ; 20(5-6): 303-309. doi: 10.1080/21678421.2019.1587634 (Year: 2019).*
Dorst et al. "Disease-modifying and symptomatic treatment of amyotrophic lateral sclerosis." Therapeutic Advances in Neurological Disorders. 2018;11. doi: 10.1177/1756285617734734 (Year: 2018).*
Mackenzie et al. "Pathological TDP-43 distinguishes sporadic amyotrophic lateral sclerosis from amyotrophic lateral sclerosis with SOD1 mutations". (2007). Ann Neurol., 61: 427-434.doi: 10.1002/ana.21147 (Year: 2007).*
Taylor et al. "Decoding ALS: From Genes to Mechanism". Nature. Nov. 10, 2016;539(7628):197-206. doi: 10.1038/nature20413 (Year: 2016).*
De Santis et al. "FUS Mutant Human Motoneurons Display Altered Transcriptome and microRNA Pathways with Implications for ALS Pathogenesis". (2017) Stem Cell Reports, vol. 9, Issue 5, 1450-1462 (Year: 2017).*
Rasmussen, S., Roberts, P. Functional studies of microRNA based on knockdown using Locked Nucleic Acid probes. Nat Methods 4, iii-iv (2007). doi: 10.1038/nmeth1034 (Year: 2007).*
Horwich et al. "Design and Delivery of Antisense Oligonucleotides to Block microRNA Function in Cultured *Drosophila* and Human Cells". Nat Protoc. 2008;3(10):1537-1549. doi: 10.1038/nprot.2008. 145 (Year: 2008).*
Montgomery et al. "Therapeutic Inhibition of miR-208a Improves Cardiac Function and Survival During Heart Failure". Circulation, vol. 124, No. 14 (2011). doi: 10.1161/CIRCULATIONAHA.111. 030932. (Year: 2011).*
Robertson B, Dalby AB, Karpilow J, Knvorova A, Leake D, Vermeulen A. Specificity and functionality of microRNA inhibitors. Silence. 2010;1(1):10. Published Apr. 1, 2010. doi:10.1186/1758-907X-1-10 (Year: 2010) (Year: 2010).*
Dupuis et al. "A Randomized, Double Blind, Placebo-Controlled Trial of Pioglitazone in Combination with Riluzole in Amyotrophic Lateral Sclerosis". PLoS One. 2012;7(6):e37885. doi: 10.1371/journal.pone.0037885. Epub Jun. 8, 2012 (Year: 2012).*
Cudkowicz et al. "Dexpramipexole versus placebo for patients with amyotrophic lateral sclerosis (EMPOWER): a randomised, double-blind, phase 3 trial". Lancet Neurol. Nov. 2013;12(11):1059-67. doi: 10.1016/S1474-4422(13)70221-7 (Year: 2013).*
(Continued)

*Primary Examiner* — Brian Whiteman
*Assistant Examiner* — Amanda M Zahorik
(74) *Attorney, Agent, or Firm* — Lucas & Mercanti, LLP

(57) ABSTRACT

The present invention relates to an inhibitor of miR-129, relative compounds and pharmaceutical compositions for use in the treatment and/or prevention of amyotrophic lateral sclerosis and Alzheimer's disease. The invention also relates to a method for the diagnosis and/or prognosis of Alzheimer's disease in a subject or to identify a subject at risk to develop amyotrophic lateral sclerosis or Alzheimer's disease and to a method for the measuring the efficacy of a therapy for amyotrophic lateral sclerosis or for Alzheimer's disease and relative kits.

5 Claims, 7 Drawing Sheets

Figure 1:
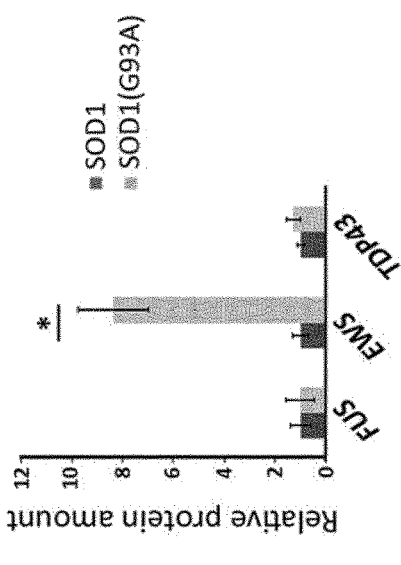
Figure 1:
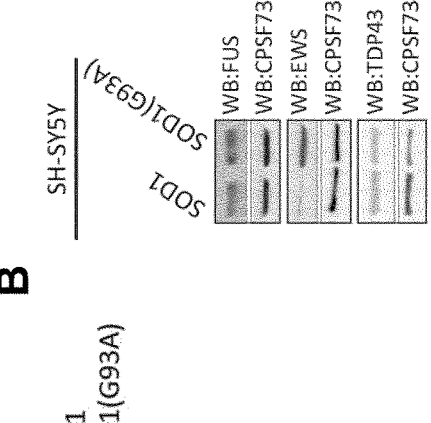
Figure 1:
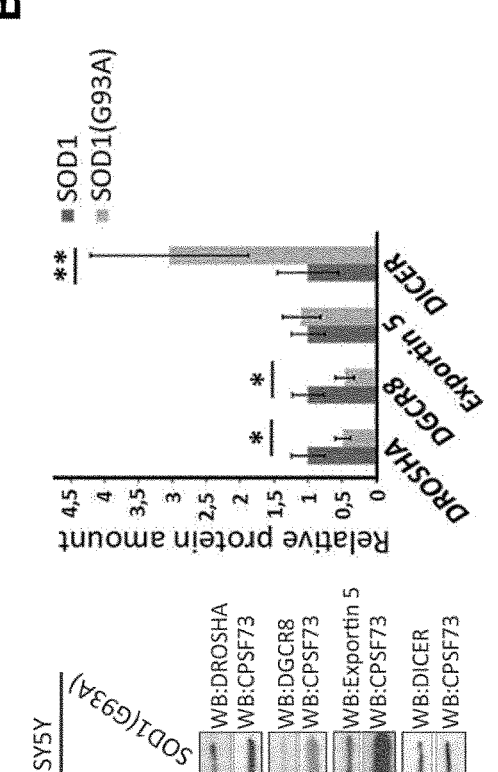
Figure 1:
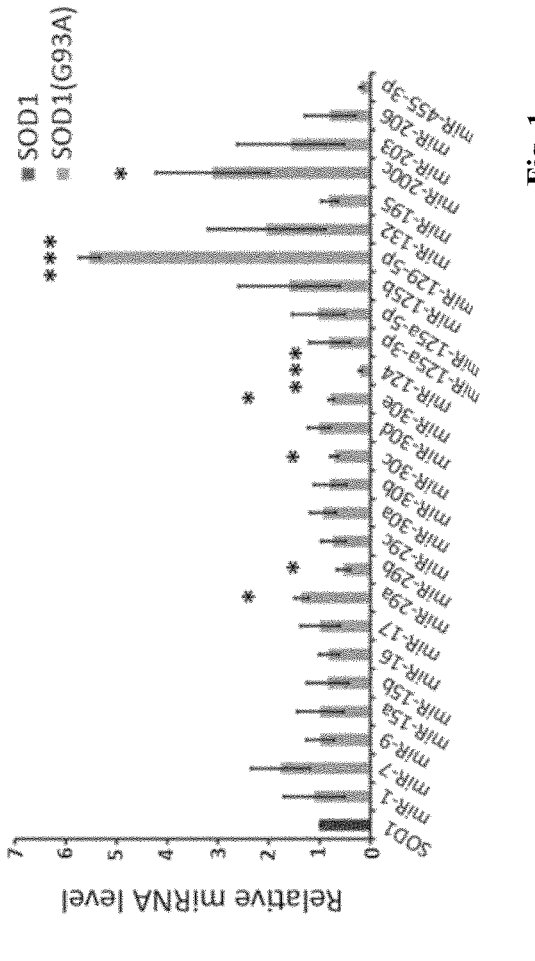

Specification includes a Sequence Listing.

(56)                    References Cited

OTHER PUBLICATIONS

A Loffreda, "RNA Metabolism alteration in amyotrophic lateral sclerosis models", Jul. 15, 2014 (Jul. 15, 2014), Retrieved from the Internet: URL:https://boa.unimib.it/retrieve/handle/10281/81488/120391/PhD_unimib_744988.pdf [retrieved on Dec. 11, 2019] (189 pages).

Zhilei Zeng; et al, "MicroRNA-129-5p alleviates nerve injury and inflammatory response of Alzheimer's disease via downregulating SOX6", Cell Cycle, vol. 18, No. 22, Sep. 29, 2019 (Sep. 29, 2019), pp. 3095-3110.

L Tremolizzo; et al, "Micrornas in als: from molecular mechanisms to clinical relevance", Jul. 9, 2014 (Jul. 9, 2014), Retrieved from the Internet: URL:https://boa.unimib.it/handle/10281/51367 [retrieved on Dec. 12, 2019] (Abstract only, 1 page).

Ellis Patrick; et al, "Dissecting the role of non-coding RNAs in the accumulation of amyloid and tau neuropathologies in Alzheimer's disease", Molecular Neurodegeneration, vol. 12, No. 1, Jul. 1, 2017 (Jul. 1, 2017) (13 pages).

Oleg Butovsky; et al., "Targeting miR-155 restores abnormal microglia and attenuates disease in SOD1 mice", Annals of Neurology, vol. 77, No. 1, Jan. 27, 2015 (Jan. 27, 2015), pp. 75-99.

Alessia Loffreda; et al, "miR-129-5p: A key factor and therapeutic target in amyotrophic lateral sclerosis", Progress in Neurobiology, Apr. 1, 2020 (Apr. 1, 2020), p. 101803 (12 pages).

Saeedeh Hosseinian; et al, "A meta-analysis of gene expression data highlights synaptic dysfunction in the hippocampus of brains with Alzheimer's disease", Scientific Reports, vol. 10, No. 1, May 20, 2020 (May 20, 2020) (9 pages).

ISA/EPO, "International Search Report and Written Opinion", issued in connection with PCT International Application No. PCT/EP2020/058571 and mailed Jun. 17, 2020 (20 pages).

* cited by examiner

INHIBITOR OF miR-129 AND USES THEREOF

CROSS-REFERENCE TO RELATED APPLICATIONS

This application is a 371 of PCT/EP2020/058571, filed Mar. 26, 2020, which claims the benefit of Italian Patent Application No. 102019000004571, filed Mar. 27, 2019.

REFERENCE TO A SEQUENCE LISTING SUBMITTED ELECTRONICALLY VIA EFS-WEB

The content of the electronically submitted sequence listing, file name: 128-1251_SeqListing.txt; size: 8.2 kb; and date of creation: Sep. 27, 2021, filed herewith, is incorporated herein by reference in its entirety.

TECHNICAL FIELD

The present invention relates to an inhibitor of miR-129, relative compounds and pharmaceutical compositions for use in the treatment and/or prevention of amyotrophic lateral sclerosis and Alzheimer's disease. The invention also relates to a method for the diagnosis and/or prognosis of Alzheimer's disease in a subject or to identify a subject at risk to develop amyotrophic lateral sclerosis or Alzheimer's disease and to a method for the measuring the efficacy of a therapy for amyotrophic lateral sclerosis or for Alzheimer's disease and relative kits.

INTRODUCTION

Amyotrophic lateral sclerosis (ALS) is a relentless neurodegenerative disease without effective therapeutic options. Phenotypic variability and lack of predictive models are major issues in ALS and the need for state biomarkers is therefore high. Furthermore, despite the considerable amount of data obtained on the pathogenic mechanisms derived from different models, a common pathophysiological mechanism that could allow a tangible therapeutic advance remains to be identified.

The genetic and environmental causes of ALS are still under investigation, but 90% of ALS cases are classified as sporadic. So far, only about 10% of patients have a familial history (Chia et al, 2018; Renton et al, 2014). The best-studied genetic cause of ALS are mutations in or deletion of the Cu/Zn Super Oxide Dismutase 1 (SOD1) gene (Rosen et al, 1993). Only recently, with advanced genomic screening tools, several other genes associated to ALS have been identified including TAR DNA-binding protein 43 kDa (TARDBP), Fused in Sarcoma (FUS), and C90RF72 (De-Jesus-Hernandez et al, 2011; Kabashi et al, 2008; Kwiatkowski et al, 2009; Sreedharan et al, 2008; Vance et al, 2009; Yokoseki et al, 2008). While C90RF72 has been identified as the most prevalent mutated gene among ALS patients, with 40% of fALS patients carrying a mutation in this gene (Majounie et al, 2012), the abundance and variety of identified SOD1 mutations, which account for 20% of the fALS cases, have made this a widespread experimental paradigm (Renton et al, 2014).

Interestingly, TDP-43 and FUS are RNA-binding proteins that function in mRNA and miRNA biogenesis (Buratti et al, 2010; Kawahara & Mieda-Sato, 2012; Morlando et al, 2012). MiRNAs are small non-coding RNAs that regulate eukaryotic gene expression at the post-transcriptional level, mainly exerting a repressive function by governing the translation and degradation of mRNA targets (Loffreda et al, 2015). Several observations support the significance of miRNAs in neuronal physiology (reviewed in (Sun et al, 2013)). Importantly, the disruption of miRNA expression in Purkinje cells by postnatal ablation of DICER, a crucial miRNA maturation factor, was shown to lead to neurodegeneration (Schaefer et al, 2007), supporting an essential role of miRNAs in the survival of differentiated post-mitotic neurons. Moreover, evidence is accumulating for a critical role of specific miRNAs in neurodegenerative disorders, as in the case of miR-206/miR-153 in Alzheimer's disease (Lee et al, 2012; Liang et al, 2012) or miR-9/miR-9* in Huntington's disease (Packer et al, 2008). MiRNA expression has also been repeatedly investigated in motor neuron diseases (Butovsky et al, 2015; Emde et al, 2015; Haramati et al, 2010; Parisi et al, 2016; Williams et al, 2009), including ALS, where a global reduction of mature miRNAs and alterations in miRNA processing was found in post-mortem spinal cord samples of patients (Figueroa-Romero et al, 2016). In addition, specific miRNAs were found to be dysregulated in the cerebrospinal fluid, serum and leukocytes of ALS patients (Benigni et al, 2016; De Felice et al, 2014; Freischmidt et al, 2015; Takahashi et al, 2015; Tasca et al, 2016).

Because of their role as regulators of multiple biological processes miRNAs have gained increasing attention as obvious potential novel candidates biomarkers (Cloutier et al, 2015; Galimberti et al, 2014; Gaughwin et al, 2011; Keller et al, 2011; Miyachi et al, 2010) and therapeutic targets. Currently, several microRNAs-based therapeutic strategies are being investigated for the treatment of human cancers. Similar approaches could be envisaged for neurodegenerative diseases, although delivery to the CNS represents an additional challenge. Two miRNA-based therapeutic strategies are being explored in vivo: the restoration of miRNA expression using miRNA mimics, and the inhibition with anti-miRNA molecules in order to create a loss-of-function in the miRNA of interest. Nevertheless, the recent FDA approval of an antisense oligonucleotide-based therapeutic strategy for spinal muscular atrophy (SMA) provides a successful model of intervention for other motor neuron diseases, including ALS (Parente et al., 2018).

Alzheimer's disease (AD), also referred to simply as Alzheimer's, is a chronic neurodegenerative disease that usually starts slowly and gradually worsens over time. It is the cause of 60-70% of cases of dementia. The most common early symptom is difficulty in remembering recent events. As the disease advances, symptoms can include problems with language, disorientation (including easily getting lost), mood swings, loss of motivation, not managing self-care, and behavioural issues. Gradually, bodily functions are lost, ultimately leading to death. Although the speed of progression can vary, the typical life expectancy following diagnosis is three to nine years.

The cause of Alzheimer's disease is poorly understood. About 70% of the risk is believed to be inherited from a person's parents with many genes usually involved. Other risk factors include a history of head injuries, depression, and hypertension. The disease process is associated with plaques and neurofibrillary tangles in the brain. A probable diagnosis is based on the history of the illness and cognitive testing with medical imaging and blood tests to rule out other possible causes. Initial symptoms are often mistaken for normal ageing. Examination of brain tissue is needed for a definite diagnosis. There are no medications or supplements that have been shown to decrease risk. No treatments stop or reverse its progression, though some may temporarily improve symptoms.

Therefore, there is still the need for diagnostic and therapeutic tools for ALS and AD.

SUMMARY OF THE INVENTION

The present invention identifies miR-129 as relevant small non-coding RNA molecule in ALS and AD in terms of pathological hallmarks and for therapeutic intervention.

MiR-129-5p is one of the two mature microRNAs that originate from the opposite arms of the miR-129 precursor, miR-129-1. MiR129-5p expression was consistently increased in different models of SOD1-linked ALS and in peripheral blood mononuclear cells (PBMCs) of sporadic ALS patients as well as in samples from Alzheimer's disease subjects. The inventors demonstrate that miR129-5p targets the mRNA for the mammalian ELAVL4/HuD, which codes for an RNA-binding protein that is predominantly expressed in neurons where it controls splicing, translation, localization, and stability of several important neuronal mRNAs (reviewed in (Bronicki & Jasmin, 2013)). Importantly, the inventors show that administration of an antisense oligonucleotide inhibitor of miR-129-5p to SOD1G93A mice extended survival, rescued body weight and grip strength loss, and improved neuromuscular phenotype in treated mice. These findings identify miR-129 as a promising therapeutic target for ALS.

Therefore, the present invention provides at least one compound selected from the group consisting of:
- a) an inhibitor of miR-129;
- b) a polynucleotide coding for the compound a);
- c) a recombinant expression vector comprising said polynucleotide;
- d) a host cell genetically engineered expressing said polynucleotide,
for use in the treatment and/or prevention of amyotrophic lateral sclerosis.

The invention also provides at least one compound selected from the group consisting of:
- a) an inhibitor of miR-129;
- b) a polynucleotide coding for the compound a);
- c) a recombinant expression vector comprising said polynucleotide;
- d) a host cell genetically engineered expressing said polynucleotide,
for use in the treatment and/or prevention of Alzheimer's disease.

Preferably the compound is a nucleic acid molecule.

Preferably the inhibitor is selected from: a single-stranded or double-stranded nucleic acid molecule, an siRNA molecule, an antisense oligonucleotide, derivatives and mixtures thereof.

Still preferably the nucleic acid molecule has sufficient complementarity to miR-129 to form a hybrid under physiological conditions.

Preferably the inhibitor is a nucleic acid molecule comprising at least 20 nucleotides complementary to at least one sequence selected from SEQ ID NO: 1 or SEQ ID NO: 2 or a variant thereof.

Still preferably the inhibitor is a nucleic acid molecule having at least 85% complementarity to at least one sequence selected from SEQ ID NO: 1 or SEQ ID NO: 2, or a variant thereof.

Still preferably the inhibitor comprises the sequence SEQ ID NO: 1 or SEQ ID NO: 2, or a variant thereof, preferably said inhibitor has essentially the sequence of SEQ ID NO: 1 or SEQ ID NO: 2 or a variant thereof.

The invention also provides a pharmaceutical composition comprising at least one compound as defined above and excipients and/or adjuvants for use in the treatment and/or prevention of amyotrophic lateral sclerosis or for use in the treatment and/or prevention of Alzheimer's disease.

Preferably the inhibitor as defined above is comprised in a vector.

The invention further provides a method for the diagnosis and/or prognosis of Alzheimer's disease in a subject or to identify a subject at risk to develop Alzheimer's disease comprising the following steps:
- a) measuring the amount of miR-129 and/or miR-30 and/or miR-200 in a biological sample isolated from the subject, and
- b) comparing the measured amount of step a) with an appropriate control amount of miR-129 and/or miR-30, wherein if the amount of miR-129 and/or miR-30 and/or miR-200 in the biological sample is higher than the control amount, this indicates that the subject is affected by amyotrophic lateral sclerosis or is at risk of developing amyotrophic lateral sclerosis.

Preferably the amounts of miR-129 and miR-30 are measured, or the amounts of miR-129 and miR-200 are measured or the amounts of miR-200 and miR-30 are measured, or the amounts of miR-129, miR-30 and miR-200 are measured.

Preferably the biological sample is a blood sample.

The invention further provides a method for measuring the efficacy of a therapy for amyotrophic lateral sclerosis or for Alzheimer's disease comprising the following steps:
- a) measuring the amount of miR-129 in a biological sample isolated from a treated subject, and
- b) comparing the measured amount of step a) with an appropriate control amount of miR-129.

The method for measuring the efficacy of a therapy for Alzheimer's disease may further comprise the following steps:
- a1) measuring the amount of miR-30 in a biological sample isolated from a treated subject, and
- b1) comparing the measured amount of step a) with an appropriate control amount of miR-30 and/or
- a2) measuring the amount of miR-200 in a biological sample isolated from a treated subject, and
- b2) comparing the measured amount of step a) with an appropriate control amount of miR-200.

Preferably the amounts of miR-129 and miR-30 are measured, or the amounts of miR-129 and miR-200 are measured or the amounts of miR-200 and miR-30 are measured, or the amounts of miR-129, miR-30 and miR-200 are measured.

The invention further provides a kit for the diagnosis and/or prognosis of Alzheimer's disease or for measuring the efficacy of a therapy for amyotrophic lateral sclerosis or for Alzheimer's disease comprising:
- means to detect and/or measure the amount of miR-129 and/or miR-30 and/or miR-200; and optionally
- control means.

Still preferably the inhibitor is a nucleic acid molecule comprising at least 20 nucleotides complementary to at least one sequence selected from miR129-1 microRNA 129-1 [*Homo sapiens* (human)] Gene ID: 406917 GGAUC-UUUUUGCGGUCUGGGCUUGCUGUUCCUCUCAAC-AGUAGUCAGGAA GCCCUUACCCCAAAA-AGUAUCU (SEQ ID NO: 1) or a variant thereof or miR-

5

129-5p (NCBI MIMAT0000242)
CUUUUUGCGGUCUGGGCUUGC (SEQ ID NO: 2).

In the present invention by miR-129, it is intended miR-129 in all its forms, including the miR-129 precursor, miR-129-1 and miR129-5p and variants thereof. Preferred miR-129-1 is miR-129-5p.

```
        hsa-mir-129-1 MI0000252
                              (SEQ ID NO. 1)
        GGAUCUUUUGCGGUCUGGGCUUGCU

GUUCCUCUCAACAGUAGUCAGGAAGC

CCUUACCCCAAAAAGUAUCU hsa-miR-129-5p MIMAT0000242
                              (SEQ ID NO. 2)
        CUUUUUGCGGUCUGGGCUUGC
```

In the present invention by miR-30, it is intended miR-30 in all its forms, including the miR-30 precursor, miR-30a, miR-30b, miR-30c, miR-30d, miR-30e and variants thereof. Preferred miR-30 is miR-30c.

In the present invention by miR-200, it is intended miR-200 in all its forms, including the miR-200 precursor, miR-200a, miR-200b, miR-200c, miR-141, miR-429 and variants thereof. Preferred miR-200c.

Then, the present invention provides an inhibitor of miR-129 for use in the treatment of amyotrophic lateral sclerosis. Preferably said inhibitor is a small molecule, an inhibitory nucleic acid agent or a genome editing agent. An editing agent is an agent which can mediate targeted gene disruption or repair, wherein said agent is an engineered nuclease, for instance a Zn Finger nuclease, a transcription activator-like effector nuclease, or a clustered regularly interspaced short palindromic repeats system.

Preferably the inhibitory nucleic acid agent is selected from the group consisting of: siRNA, an antisense oligonucleotide (e.g. an ASO with phosphothiorate or morpholino chemistry, an antagomir, an LNA), a miRNA sponge, and/or a ribozyme.

Still preferably the inhibitor of miR-129-1 comprises at least one sequence complementary to miR-129-1 and/or miR-129-5p. Preferably the inhibitor of miR-129-1 and/or miR-129-5p comprises at least one sequence complementary to SEQ ID NO. 1 or SEQ ID NO. 2 or comprises SEQ ID NO. 1 or SEQ ID NO. 2. Preferably said inhibitor reduces the function and/or activity of miR-129-1 and/or miR-129-5p.

More preferably said inhibitor has at least one property selected from the group consisting of: inhibiting the miRNA activity, preferably inhibiting mRNA target binding, increasing mRNA levels of at least one specific miR-129-1 and/or miR-129-5p target, an antisense oligonucleotide inhibitor of miR-129-5p, extending survival of SOD1G93A mice, rescuing body weight loss and/or grip strength loss and/or improving neuromuscular phenotype in ALS affected subjects (human or animals).

In a preferred embodiment said miRNA sponge has the formula:

(X1sX2sX3)n1S2(X1sX2sX3)n2 wherein
X1, X2 and X3 are independently chosen from
a sequence complementary to miR-129-1 and/or miR-129-5p, preferably modified from nucleotide 9 to nucleotide 12 to create a bulge;

X3 may be present or absent;
s is a Spacer sequence of 4 to 6 nucleotides, preferably 4 nucleotides;
S2 is a central Spacer sequence of 4 to 6 nucleotides, preferably 6 nucleotides, preferably corresponding to a restriction enzyme site, preferably a site for the XbaI restriction enzyme;
n1 and n2 is a number independently selected from 3, 6 and 24, preferably between 3, 6 and 12, most preferably n is 3, nI and n2 may be identical or different.

In a preferred embodiment said miRNA sponge has the formula:

(AsB)n1S2(AsB)n2 wherein:
A is a sequence complementary to miR-129-1 and/or miR-129-5p, preferably modified from nucleotide 9 to nucleotide 12 to create a bulge;
B is a sequence complementary to miR-129-1 and/or miR-129-5p, preferably modified from nucleotide 9 to nucleotide 12 to create a bulge;
S is a Spacer sequence of 4 to 6 nucleotides, preferably 4 nucleotides;
S2 is a central Spacer sequence of 4 to 6 nucleotides, preferably 6 nucleotides, preferably corresponding to a site for a restriction enzyme, preferably the Xba I restriction enzyme
n1 and n2 is a number independently selected from 3, 6 and 24, preferably between 3, 6 and 12, most preferably n is 3, n1 and n2 may be identical or different.

Preferably the sequence of the inhibitor further comprises one or more locked nucleic acid (LNA) nucleotides and one or more non-locked nucleotides, wherein at least one of the non-locked nucleotides comprises a chemical modification, preferably the locked nucleic acid (LNA) nucleotides has a 2' to 4' methylene bridge, preferably the chemical modification is a 2' O-alkyl or 2' halo modification.

Still preferably said inhibitor of miR-129 is used with at least one additional agent.

Preferably the additional agent is selected from the group consisting of: an inhibitor of sodium channels, an inhibitor of kainite receptor, an inhibitor of NMDA receptors, an antioxidant, an antisense oligonucleotide against ALS causative genes such as SOD1 and/or C90RF72, Preferably the additional agent is selected from:
Riluzole The mechanisms of Riluzole action in ALS patients is not completely defined. Riluzole inhibits TTX-sensitive sodium channels, the kainate and NMDA receptors which are linked to excitotoxicity neuronal death. The drug has also been demonstrated to postsynaptically potentiate GABAA receptors with a possible neuroprotective effect.
Edaravone The mechanism by which edaravone might be effective in ALS is not known.] The drug is acts as an antioxidant, and oxidative stress has been hypothesized to involved in motor neuron degeneration in ALS patients.
ASO Antisense oligonucleotides against ALS causative genes like SOD1 and/or C90RF72 are under evaluation in Phase 1 to 3 clinical trials.

More preferably said at least one additional agent is an inhibitor of miR-129-1 as defined above and in the present invention.

Then the use refers to a combination of one or more inhibitor of miR-129-1, i.e one or more siRNA, an antisense oligonucleotide (e.g. an antagomir, an LNA), a miRNA sponge, and/or a ribozyme that can be the same or different.

In a preferred aspect, the inhibitor as above defined is a nucleic acid molecule comprising at least 20 nucleotides complementary to at least one sequence selected from SEQ ID NO: 1 or 2 or a variant thereof.

In another preferred aspect, the inhibitor as above defined is a nucleic acid molecule having at least 85% complementarity to at least one sequence selected from SEQ ID NO: 1 or 2 or a variant thereof.

In another preferred embodiment, the inhibitor as above defined comprises the sequence SEQ ID NO: 1 or SEQ ID NO: 2 or a variant thereof, more preferably said inhibitor has essentially the sequence of SEQ ID NO: 1 or SEQ ID NO: 2.

The inhibitor of the invention also comprises the corresponding RNA sequences of the above defined inhibitors.

In a yet preferred embodiment, the inhibitor as above defined is a nucleic acid molecule having 100% complementarity to at least one sequence selected from SEQ ID NO: 1 or 2.

Preferably, the inhibitor as above defined has essentially the following sequences: 5'-ACAGCAAGCCCA-GACCGCAAAAAGA-3' (SEQ ID NO: 3)

The miRNA-129 and/or a miRNA-129-5p molecule, an equivalent or the source thereof as above defined is preferably characterized by being an oligonucleotide comprising at least 20 nucleotides of any of the sequences SEQ ID NO: 1 or SEQ ID NO: 2 or a variant thereof.

In the present invention a nucleic acid molecule that has sufficient complementarity to a miR to form a hybrid under physiological conditions is e.g. a nucleic acid molecule which is at least 85% complementary to the sequence of the above miR.

In the context of the present invention, physiological conditions are preferably a temperature range of 20-40° C. and/or atmospheric pressure of 1 and/or pH of 6-8 and/or glucose concentration of 1-20 mM and/or atmospheric oxygen concentration.

In the present invention miR inhibitors and/or antagomirs are chemically engineered oligonucleotides which are used to silence endogenous microRNAs. An antagomir is a small synthetic RNA that is perfectly complementary to the specific miRNA target with either mispairing at the cleavage site of Ago2 or some sort of base modification to inhibit Ago2 cleavage. Usually, antagomirs have some sort of modification to make it more resistant to degradation. It is unclear how antagomirization (the process by which an antagomir inhibits miRNA activity) operates, but it is believed to inhibit by irreversibly binding the miRNA. Antagomirs are used to constitutively inhibit the activity of specific miRNAs.

In the context of the present invention, the variants of the sequence of SEQ ID NO:1 or 2 are preferably at least 85%, preferred 90% and more preferred 95% homologue to the SEQ ID NO: 1 or 2. This means that in the variants e.g. up to three nucleotides can be replaced by other nucleotides, preferably only two and more preferred only one nucleotide is replaced. The term homology is understood as identity. This means that e.g. at least 85% of the nucleotides are identical whereas the remainder of the nucleotides may be changed.

Variants may also comprise the above-mentioned sequences and a modified oligonucleotide conjugated to one or more moieties which enhance the activity, cellular distribution or cellular uptake of the resulting antisense oligonucleotides. A preferred moiety is a cholesterol moiety or a lipid moiety. Additional moieties for conjugation include carbohydrates, phospholipids, biotin, phenazine, folate, phenanthridine, anthraquinone, acridine, fluoresceins, rhodamines, coumarins, and dyes. In certain variants, a conjugate group is attached directly to a modified oligonucleotide. In certain variants, a conjugate group is attached to a modified oligonucleotide by a linking moiety selected from amino, hydroxyl, carboxylic acid, thiol, unsaturations (e.g., double or triple bonds), 8-amino-3,6-dioxaoctanoic acid (ADO), succinimidyl 4-(N-maleimidomethyl) cyclohexane-1-carboxylate (SMCC), 6-aminohexanoic acid (ALEX or AHA), substituted C1-C10 alkyl, substituted or un-substituted C2-C10 alkenyl, and substituted or un-substituted C2-C10 alkynyl. In certain variants, a substituent group is selected from hydroxyl, amino, alkoxy, carboxy, benzyl, phenyl, nitro, thiol, thioalkoxy, halogen, alkyl, aryl, alkenyl and alkynyl. In certain variants, the compound comprises a modified oligonucleotide having one or more stabilizing groups that are attached to one or both termini of a modified oligonucleotide to enhance properties such as, for example, nuclease stability. Included in stabilizing groups are cap structures. These terminal modifications protect a modified oligonucleotide from exonuclease degradation and can help in delivery and/or localization within a cell. The cap can be present at the 5'-terminus (5'-cap), or at the 3'-terminus (3'-cap) or can be present on both termini. Cap structures include, for example, inverted deoxy abasic caps.

Suitable cap structures include a 4',5'-methylene nucleotide, a 1-(beta-D-erythrofuranosyl) nucleotide, a 4'-thio nucleotide, a carbocyclic nucleotide, a 1,5-anhydrohexitol nucleotide, an L-nucleotide, an alpha-nucleotide, a modified base nucleotide, a phosphorodithioate linkage, a threo-pentofuranosyl nucleotide, an acyclic 3',4'-seco nucleotide, an acyclic 3,4-dihydroxybutyl nucleotide, an acyclic 3,5-dihydroxypentyl nucleotide, a 3'-3'-inverted nucleotide moiety, a 3'-3'-inverted abasic moiety, a 3'-2-inverted nucleotide moiety, a 3'-2-inverted abasic moiety, a 1,4-butanediol phosphate, a 3'-phosphoramidate, a hexylphosphate, an aminohexyl phosphate, a 3'-phosphate, a 3'-phosphorothioate, a phosphorodithioate, a bridging methylphosphonate moiety, and a non-bridging methylphosphonate moiety 5'-amino-alkyl phosphate, a 1,3-diamino-2-propyl phosphate, 3-aminopropyl phosphate, a 6-aminohexyl phosphate, a 1,2-aminododecyl phosphate, a hydroxypropyl phosphate, a 5'-5'-inverted nucleotide moiety, a 5'-5'-inverted abasic moiety, a 5'-phosphoramidate, a 5'-phosphorothioate, a 5'-amino, a bridging and/or non-bridging 5'-phosphoramidate, a phosphorothioate, and a 5'-mercapto moiety.

The compounds as above defined can be provided within a delivery vehicle, optionally wherein the delivery vehicle is selected from a viral vector, microspheres, liposomes, colloidal gold particles, lipopolysaccharides, polypeptides, polysaccharides, or pegylation of viral vehicles. Preferably they are introduced into the body of the person to be treated as a nucleic acid within a vector which replicates into the host cells and produces the oligonucleotides.

As used herein, the term "host cell genetically engineered" relates to host cells which have been transduced, transformed or transfected with the polynucleotide or with the vector described previously. As representative examples of appropriate host cells, one can cite bacterial cells, such as *E. coli, Streptomyces, Salmonella typhimurium*, fungal cells such as yeast, insect cells such as Sf9, animal cells such as CHO or COS, plant cells, etc. The selection of an appropriate host is deemed to be within the scope of those skilled in the art from the teachings herein. Preferably, said host cell is an animal cell, and most preferably a human cell. The introduction of the polynucleotide or of the vector described previously into the host cell can be performed by method well known from one of skill in the art such as calcium phosphate transfection, DEAE-Dextran mediated transfection, or electroporation. The polynucleotide may be a vector such as for example a viral vector. Another object of the invention is a composition comprising a transformed host cell expressing the compound as above defined. The man skilled in the art is well aware of the standard methods for incorporation of a polynucleotide into a host cell, for example transfection, lipofection, electroporation, microinjection, viral infection, thermal shock, transformation after chemical permeabilisation of the membrane or cell fusion.

In the present invention, the antisense oligonucleotides are preferably antisense DNA- and/or RNA-oligonucleotides, and the derivatives of the antisense oligonucleotide are e.g. modified antisense oligonucleotide as e.g. antisense 2'-O-methyl oligo-ribonucleotides, antisense oligonucleotides containing phosphorothiaote linkages, antisense oligonucleotides containing Locked Nucleic Acid LNA(R) bases, morpholino antisense oligonucleotides, PPAR-gamma agonists, antagomirs.

Since miRNAs target their mRNA by Watson-Crick base-pairing it is preferred that the inhibitor of miR-129-1 and/or miR-129-5p is an antisense oligonucleotide, which is complementary to the miRNA and base pairs with the miRNA in competition with the endogenous mRNA target. For the purpose of the invention, the sequence of the antisense oligonucleotide is 50% identical to the complement of miR-129-1 and/or miR-129-5p and/or its seed sequence, preferably 60%, 70%, 80%, 90%, or 95% and most preferably 100% identical to the complement of the miR-129-1 and/or miR-129-5p and/or its seed sequence. Moreover, particularly preferred are antisense oligonucleotides which are chemically modified to improve the thermal stability of the duplex between the antisense oligonucleotide and the miRNA. Preferred chemical modifications comprise, for example, bicyclic high-affinity RNA analogues in which the furanose ring in the sugar-phosphate backbone is chemically locked in an RNA mimicking N-type conformation by the introduction of 2'-0,4'-C-methylene bridge (LNA(R)-antimiRs). Other preferred chemical modified oligonucleotides include morpholinos, 2'-O-methyl, 2'-O-methoxyethyl oligonucleotides and cholesterol-conjugated 2'-O-methyl modified oligonucleotides (antagomirs).

Inhibitors in context of the invention also comprise any substance that is able to inhibit miR-129-1 and/or miR-129-5p either by inhibiting the expression or by inhibiting the silencing function of the microRNA. Thus, any compound interfering with the microRNA pathway, for example by inhibiting the function of the proteins Pasha, Drosha, Dicer or Argonaut family proteins can be an inhibitor according to the invention.

Furthermore, any compound inhibiting the expression of the precursor microRNA of miR-129-1 and/or miR-129-5p, such as, for example inhibitors of polymerase II or III are candidate inhibitor of miRNA expression. The mature miRNA also serves as a target for the design of inhibitors of miR-129-1 and/or miR-129-5p function. Nucleic acids having perfect or mismatched complementarity to the microRNA may be used to inhibit, or to compete with the binding of the endogenous miR-129-1 and/or miR-129-5p with its target mRNA. How to design such miRNA inhibitors is well known in the art.

Inhibitors of miR-129-1 and/or miR-129-5p, modified oligonucleotide complementary to a miR miR-129-1 and/or miR-129-5p, or precursor thereof, described herein as well as miRNA miR-129-1 and/or miR-129-5p molecule, an equivalent or a source thereof may be prepared as a pharmaceutical composition, in particular for the treatment of autoimmune-immune mediated inflammatory diseases. Suitable administration routes include, but are not limited to, oral, rectal, transmucosal, intestinal, enteral, topical, suppository, through inhalation, intrathecal, intraventricular, intraperitoneal, intranasal, intraocular and parenteral (e.g., intravenous, intramuscular, intramedullary, and subcutaneous). An additional suitable administration route includes chemoembolization. In certain embodiments, pharmaceutical intrathecals are administered to achieve local rather than systemic exposures. For example, pharmaceutical compositions may be injected directly in the area of desired effect.

In certain embodiments, a pharmaceutical composition of the present invention is administered in the form of a dosage unit (e.g., tablet, capsule, bolus, etc.).

The compound as above defined may be administered as a pharmaceutical composition comprising a pharmacologically acceptable carrier and diluent. Administration may be carried out by known methods, wherein the inhibitor is introduced into the desired target cell in vitro or in vivo. Suitable administration methods include injection, viral transfer, use of liposomes, e.g. cationic liposomes, oral intake and/or dermal application.

For pharmaceutical applications, the composition may be in the form of a solution, e.g. an injectable solution, emulsion, suspension or the like. The composition may be administered in any suitable way, e.g. by injection, infusion, oral intake and/or by dermal application. The carrier may be any suitable pharmaceutical carrier. Preferably, a carrier is used which is capable of increasing the efficacy of the RNA molecules to enter the target cells. Suitable examples of such carriers are liposomes. The compound as above defined is administered in a pharmaceutically effective dosage, which may be in the range of 0.001 pg/kg body weight to 1 mg/kg body weight depending on the route of administration and the type or severity of the disease. The inhibitor of the present invention may comprise a single type of inhibitor molecule or a plurality of different inhibitor molecules, e.g. a plurality of different siRNA molecules and/or antagomirs. For example, an inhibitor of miR-129-1 and/or miR-129-5p, e.g. an antagomir, may be combined with an inhibitor of miR-129-1 and/or miR-129-5p, e.g. an antagomir.

In the context of the present invention, miR-129 and/or miR-129-5p molecules are intended as e.g. miRNA precursors or a mature miRNA.

In the context of the present invention, for a source it is intended e.g. a RNA or DNA molecule encoding for said miRNA, for said miRNA precursor, for said mature miRNA, for said miRNA mimic or equivalent.

In the context of the invention, a miRNA molecule or an equivalent or a mimic or an isomiR thereof may be a synthetic or natural or recombinant or mature or part of a mature miRNA or a human miRNA or derived from a human miRNA as further defined in the part dedicated to the general definitions. A human miRNA molecule is a miRNA molecule which is found in a human cell, tissue, organ or body fluids (i.e. endogenous human miRNA molecule). A human miRNA molecule may also be a human miRNA molecule derived from an endogenous human miRNA molecule by substitution, deletion and/or addition of a nucleotide. A miRNA molecule or an equivalent or a mimic thereof may be a single stranded or double stranded RNA molecule. Preferably a miRNA molecule or an equivalent, or a mimic thereof is from 6 to 30 nucleotides in length, preferably 12 to 30 nucleotides in length, preferably 15 to 28 nucleotides in length, more preferably said molecule has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

A miRNA molecule or an equivalent or a mimic or an isomiR thereof may have 70% identity over the whole mature sequence of the miR (SEQ ID NO: 1 or 2 or orthologous or orthologs thereof), preferably identity is at least 75%, 80%, 85%, 90%, 95%, 97%, 98%, 99% or 100%.

An equivalent of a miRNA molecule may be an isomiR or a mimic. A precursor sequence may result in more than one isomiR sequences depending on the maturation process. A mimic is a molecule which has a similar or identical activity with a miRNA molecule. In this context a similar activity is given the same meaning as an acceptable level of an activity.

Each of the miRNA molecules or equivalents or mimics or isomiRs thereof as identified herein has an acceptable level of an activity of a given miRNA they derive from. An acceptable level of an activity is preferably that said miRNA or equivalent or mimics or isomiRs thereof is still able to exhibit an acceptable level of said activity of said miRNA. An acceptable level of an activity is preferably at least 30%, 40%, 50%, 60%, 70%, 80%, 90%, 95% or 100%, or more than 100%, such as 200% or 300% or more of the activity of the miRNA they derive from.

A source of a miRNA molecule or a source of an equivalent of a miRNA molecule, mimic, isomiR may be any molecule which is able to induce the production of a miRNA molecule or of an equivalent thereof such as a mimic or isomiR as identified herein and which comprises a hairpin-like structure and/or a double stranded nucleic acid molecule. The presence of a hairpin-like structure may be assessed using the RNA shapes program (Steffen P. et al 2006) using sliding windows of 80, 100 and 120 nt or more. The hairpin-like structure is usually present in a natural or endogenous source of a miRNA molecule whereas a double-stranded nucleic acid molecule is usually present in a recombinant or synthetic source of a miRNA molecule or of an equivalent thereof.

A source of a miRNA molecule or of an equivalent or a mimic or an isomiR thereof may be a single stranded optionally within a hairpin like structure, a double stranded RNA or a partially double stranded RNA or may comprise three strands, an example of which is described in WO2008/10558. As used herein partially double stranded refers to double stranded structures that also comprise single stranded structures at the 5' and/or at the 3' end. It may occur when each strand of a miRNA molecule does not have the same length. In general, such partial double stranded miRNA molecule may have less than 75% double stranded structure and more than 25% single stranded structure, or less than 50% double stranded structure and more than 50% single stranded structure, or more preferably less than 25%, 20% or 15% double stranded structure and more than 75%, 80%, 85% single stranded structure. Alternatively, a source of a miRNA molecule or of an equivalent or a mimic or an isomiR thereof is a DNA molecule encoding a precursor of a miRNA molecule or of an equivalent or a mimic or an isomiR thereof. The invention encompasses the use of a DNA molecule encoding a precursor of a miRNA molecule that has at least 70% identity with said sequence SEQ ID NO: 1 or 2. Preferably, the identity is at least 75%, 80%, 85%, 90%, 95%, 97%, 98%, 99% or 100%. Preferably in this embodiment, a DNA molecule has a length of at least 50, 55, 60, 70, 75, 80, 85, 90, 95, 100, 130, 150, 200, 250, 300, 350, 400 nucleotides or more and has at least 70% identity with a DNA sequence as SEQ ID NO: 1 or 2, variants or orthologs thereof.

The induction of the production of a given miRNA molecule or of an equivalent thereof or of a mimic or an isomiR thereof is preferably obtained when said source is introduced into a cell using one assay as defined below. Cells encompassed by the present invention are later on defined. A preferred source of a miRNA molecule or of an equivalent thereof or of a mimic or an isomiR thereof is a precursor thereof, more preferably a nucleic acid encoding said miRNA molecule or an equivalent thereof or of a mimic or an isomiR thereof. A preferred precursor is a naturally occurring precursor. A precursor may be a synthetic or recombinant precursor.

A preferred source includes or comprises an expression construct comprising a nucleic acid, i.e. DNA encoding said precursor of said miRNA, more preferably said expression construct is a viral gene therapy vector selected from gene therapy vectors based on an adenovirus, an adeno-associated virus (AAV), a herpes virus, a pox virus and a retrovirus. A preferred viral gene therapy vector is an AAV or lentiviral vector. Other preferred vectors are oncolytic viral vectors. Such vectors are further described herein below. Alternatively, a source may be a synthetic miRNA molecule, or a chemical mimic as further defined in the part dedicated to general definitions.

The detection of the presence of a miRNA molecule or of an equivalent thereof such as a mimic or an isomiR of a miRNA molecule or equivalent thereof may be carried out using any technique known to the skilled person. The assessment of the expression level or of the presence of such molecule is preferably performed using classical molecular biology techniques such as (real time Polymerase Chain Reaction) qPCR, microarrays, bead arrays, RNAse protection analysis or Northern blot analysis or cloning and sequencing. The skilled person will understand that alternatively or in combination with the quantification of a miRNA molecule or of an equivalent thereof, the quantification of a substrate of a corresponding miRNA molecule or of an equivalent thereof of any compound known to be associated with a function of said miRNA molecule or of said equivalent thereof or the quantification of a function or activity of said miRNA molecule or of said equivalent thereof using a specific assay is encompassed within the scope of the invention.

A miRNA molecule or an equivalent thereof or a mimic or an isomiR thereof may be used as such as a naked molecule, with or without chemical modifications, or encapsulated into a particle or conjugated to a moiety. A preferred composition comprises a miRNA molecule or an equivalent thereof or a mimic or an isomiR thereof encapsulated into a nanoparticle or a liposomal structure. A miRNA molecule or equivalent thereof or a mimic or an isomiR thereof may be an aptamer-miRNA hybrid. An aptamer-miRNA is defined as a miRNA linked to an RNA (or DNA) oligonucleotide, the latter adopting a conformation that targets the aptamer-miRNA hybrid molecule to a cell-surface protein (e.g. cyclic RGD peptide (cyclic arginine(R)-glycine(G)-aspartic acid (D) peptide). The aptamer-tagged miRNA can be linked to e.g. polyethylene glycol, which increases the chimera's circulating half-life (Dassie, J. P., et al. 2009).

In the present invention, the expression "measuring the amount" can be intended as measuring the amount or concentration or level of the respective miRNA and/or DNA thereof, preferably semi-quantitative or quantitative. The term "amount", as used in the description refers but is not limited to the absolute or relative amount of miRNA and/or DNA thereof, and any other value or parameter associated with the same or which may result from these. Methods of measuring miRNA and DNA in samples are known in the art. To measure nucleic acid levels, the cells in a test sample can be lysed, and the levels of miRNA in the lysates or in RNA purified or semi-purified from lysates can be measured by any variety of methods familiar to those in the art. Such methods include hybridization assays using detectably labeled DNA or RNA probes (i.e., Northern blotting) or quantitative or semi-quantitative RT-PCR methodologies using appropriate oligonucleotide primers. The expert in the art knows how to design appropriate primers. Alternatively, quantitative or semi-quantitative in situ hybridization assays can be carried out using, for example, tissue sections, or unlysed cell suspensions, and detectably labeled (e.g., fluorescent, or enzyme-labeled) DNA or RNA probes. Additional methods for quantifying miRNA include RNA protection assay (RPA), cDNA and oligonucleotide microarrays, representation difference analysis (RDA), differential display, EST sequence analysis, and serial analysis of gene expression (SAGE).

The present invention will be illustrated by means of non-limiting examples in reference to the following figures.

FIG. 1. Dysregulation of miRNA biogenesis factors and miRNA expression in SH-SY5Y/SOD1(G93A) cells.

a. Left Panel: Representative Western blot analysis of components of the microprocessor complex in SH-SY5Y/SOD1(G93A) compared to SH-SY5Y/SOD1 cells. Right Panel: Densitometric quantifications of the levels of the indicated proteins as in Panel a. Equal amounts of total protein extracts were fractionated on SDS-PAGE. Error bars represent fold change standard deviation derived from at least three independent experiments (in particular: DROSHA N=3; DGCR8 N=7; DICER N=7; Exportin 5 N=4). Statistical significance between SOD1 (WT) and SOD1 (G93A) SH-SY5Y cells was determined by Paired Student's t-test; (*p<0.05; **p<0.01).

b. Left Panel: Representative Western blot analysis of DROSHA interacting proteins. Right Panel: Densitometric quantifications as in (A) of three independent experiments.

c. RT-qPCR validation of differentially expressed miRNAs in SH-SY5Y(SOD1G93A) cells. Expression level of each miRNA in SH-SY5Y/SOD1(G93A) is indicated relative to control SH-SY5Y/SOD1 cells. Error bars represent standard deviation derived from independent experiments performed in duplicate. Error bars represent standard deviation derived from independent experiments performed in duplicate. Statistical significance between SOD1 (WT) and SOD1 (G93A) SH-SY5Y cells was determined by Unpaired Student's t-test; (*p<0.05; p<0.01; *p<0.001).

Figure 2:
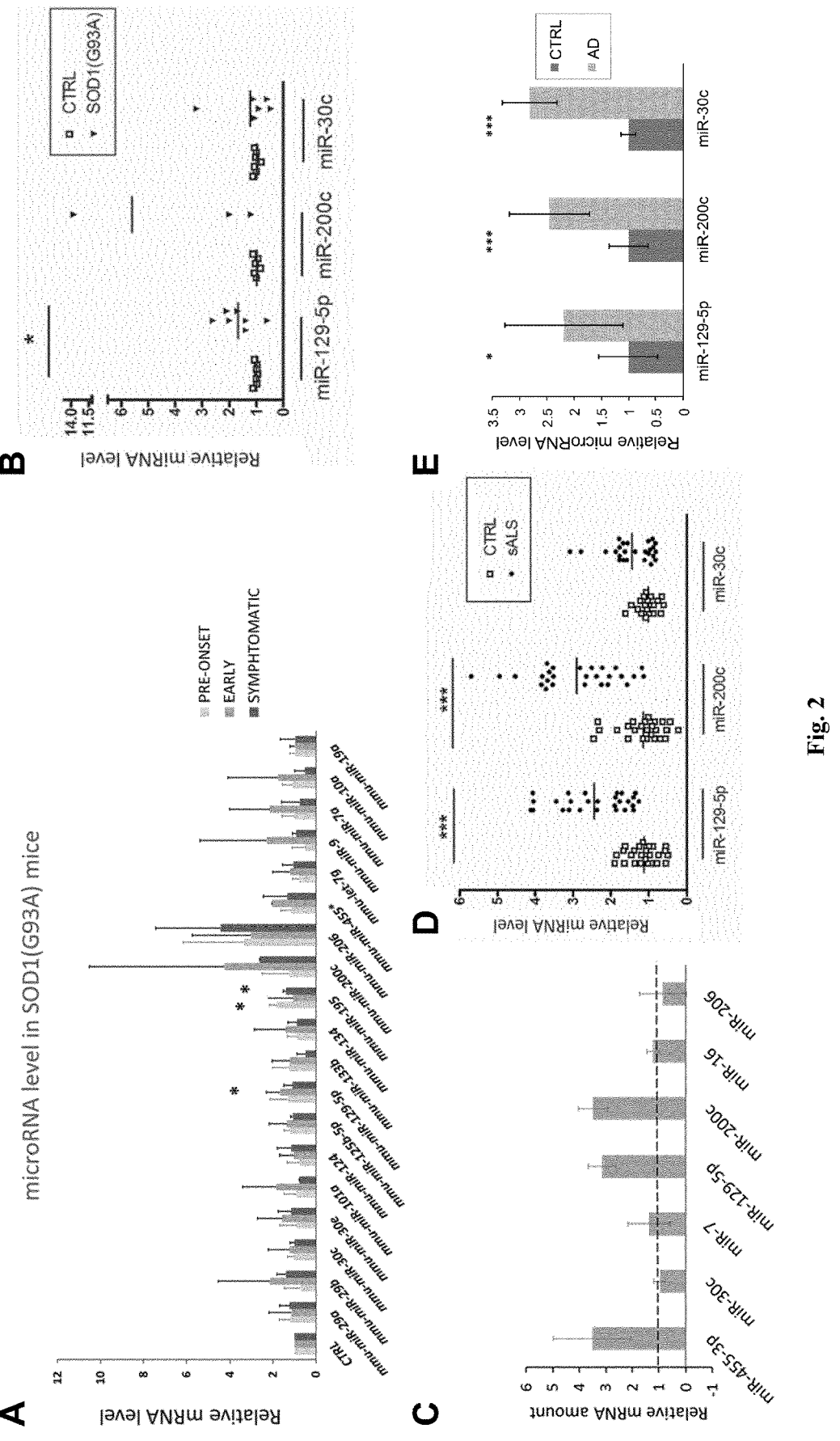

FIG. 2. MicroRNA expression level in SOD1(G93A) mice at different stages of disease and in PBMC of sporadic patients.

a. RT-qPCR analysis of 19 miRNAs in SOD1(G93A) transgenic mice at the pre-onset (<100 days, n=3), early (135 days, n=7), and symptomatic stage (140-170 days, n=3) of disease. rnu1a1 was used as internal control; for each microRNA analysed, the number of mice from which an accurate measurement was obtained is between 2 and 7.

b. RT-qPCR analysis of miRNA expression in transgenic SOD1(G93A) mice. Total RNA was extracted from the spinal cord of seven mice at early stage of disease (15 weeks) and of seven age-matched non-transgenic control mice. Relative levels of mir-129-5p, miR-200c and miR-30c were determined; rnu1a1 was used as internal control for normalization. Data are presented as box plot graphs of three technical replicates for each measurement. Statistical significance was determined using unpaired Student's t-test, * denotes p<0.05.

c. RT-qPCR analysis of miR-455-3p; miR-30c, miR-7; miR-129-5p, miR-200c; miR-16 and miR-206 in human PBMCs. Relative abundance analyzed miRNAs was measured in 7 patients with sporadic ALS and 7 control subjects. SnoRD25 and miR-16 was used as internal control.

d. RT-qPCR analysis of miR-129-5p, miR-200c, and miR-30c levels in human PBMCs. The relative abundance of these three miRNAs was measured in PBMC-extracted RNA from 27 patients with sporadic ALS (sALS) and 25 control subjects (CTRL). SnoRD25 and miR-16 were used as internal control for normalization. Statistical analysis was determined using unpaired Student's t-test (***p≤0.001).

e. RT-qPCR analysis of miR-129-5p, 200c and 30c levels in human PBMCs. The relative abundance of these three miRNAs was measured in 8 Alzheimer's Disease (AD) patients (n=7 for miR-30c) and 8 control subjects (CTRL). SnoRD25 was used as internal control for normalization. Statistical analysis was determined using unpaired Student's t-test (*p≤0.05; ***p≤0.001).

Figure 3:
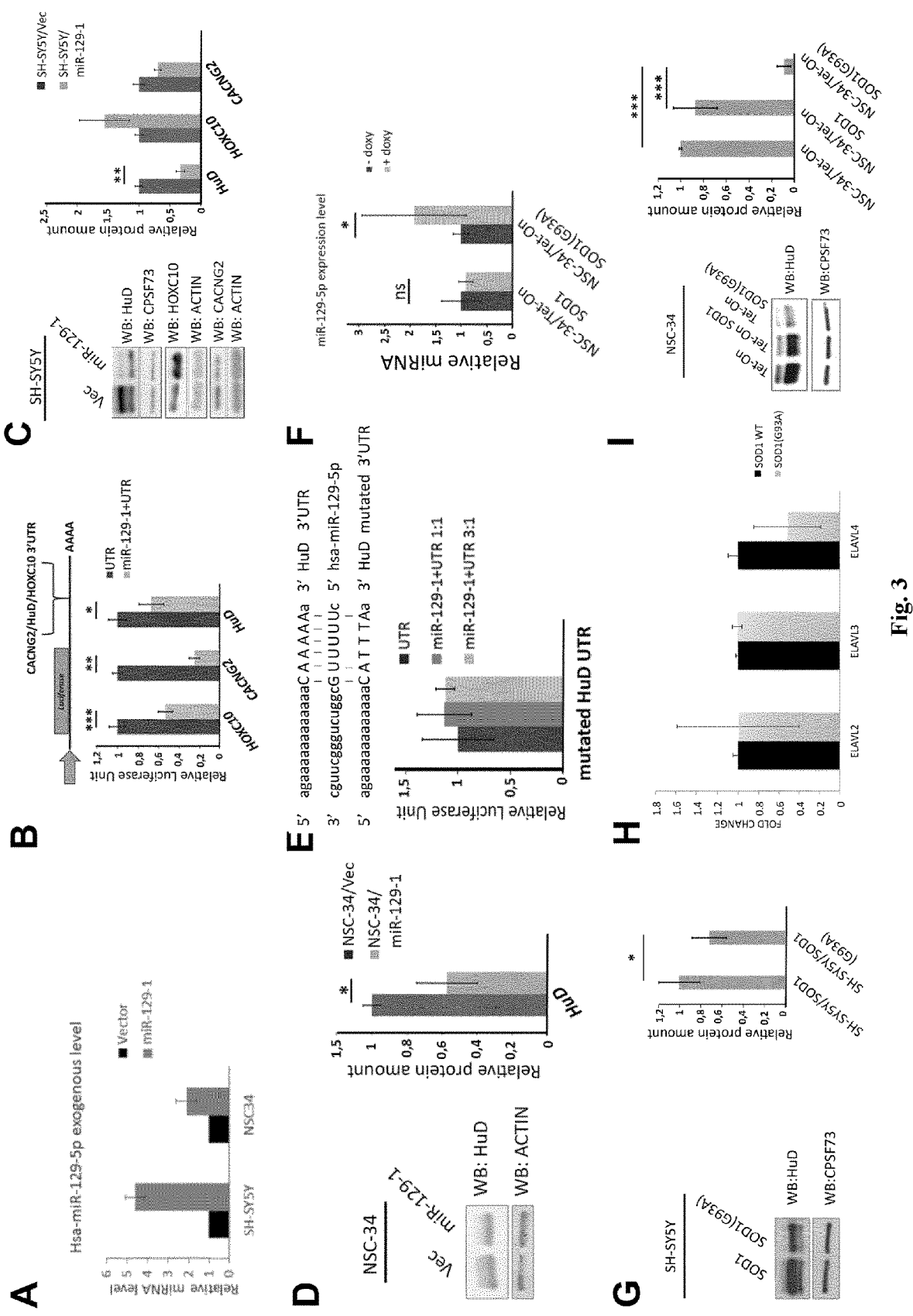

FIG. 3. HuD mRNA is a target of miR-129-5p and is downregulated in models of SOD1-linked ALS.

a. MiR-129-5p level in cellular lines stably expressing miR-129-1 precursor. RT-qPCR analysis carried out of the mature miR-129-5p in SH-SY5Y and in NSC-34 cells stably transfected with the precursor miR-129-1. SnoRD25 was used as internal control.

b. Upper panel: Schematic representation of the firefly luciferase reporter constructs depicting the insertion site of the indicated 3' UTR sequences. Lower panel: Relative firefly luciferase activity was determined in cells overexpressing miR-129-1 (grey bars) or not (black bars) and expressing firefly reporter constructs harbouring the 3' UTR of HOXC10, CACNG2 or HuD. A Renilla luciferase expressing plasmid was used as an internal transfection control. For each firefly construct, the firefly luciferase activities were normalized to Renilla luciferase activity, and the values obtained without miR-129-1 overexpression were set as 1. The mean±s.e.m. of three independent experiments is shown. Statistical significance was determined as in FIG. 1C.

c. HuD is down-regulated in models of SOD1-linked ALS. Western blot analysis of the endogenous HuD, HOXC10 and CACNG2 proteins in human SH-SY5Y cells stably expressing the precursor miR129-1. Left panel: representative Western blot. Right panel: densitometric quantification. Error bars represent fold change standard deviation derived from two independent experiments (n=3 for HuD). Statistical significance was determined by Paired Student's t-test; (**p<0.01). CPSF73 and actin were used as loading controls. Vec: cells stably transfected with the vector.

d. Western blot analysis of HuD expression in murine NSC34 cells stably transfected with either the vector (Vec) or the precursor miR129-1. Left panel: representative Western blot. Actin was used as loading control. Right panel: densitometric quantification. Error bars represent fold change standard deviation derived from three independent experiments. Statistical significance was determined by Paired Student's t-test; (*p<0.05; **p<0.01).

e. Upper panel: Schematic representation of the mutation in the miRNA (miR-129-5p) seed pairing region of HuD 3'-UTR, obtained by site-direct mutagenesis. Lower panel: Relative firefly luciferase activity was determined in cells overexpressing miR-129-1 (gray bars) or not (black bars) and expressing firefly reporter constructs harboring the mutated 3'UTRs of HuD. Luciferase activity was measured from cells transfected using two different ratios between miR-129-5p and mutated HuD and performed in three independent experiments. Statistical significance was determined by Paired Student's t-test comparing each condition with the UNTR. Sequences are reported below.

```
5' agaaaaaaaaaaaaCAAAAAa 3'  HuD 3'UTR SEQ ID NO: 40
                 ||||||
3' cguucgggucuggcGUUUUUc 5'  has-miR-129-5p SEQ ID NO: 41
                 ||    |
5' agaaaaaaaaaaaaCATTTAa 3'  HuD mutated 3'UTR SEQ ID NO: 42
``` f. RT-qPCR analysis of miR-129-5p carried out in NSC-34 cells expressing either the wild type SOD1 protein or the SOD1(G93A) mutant under a doxycycline-inducible promoter (N=6). The expression level of miR-129-5p was measured in both cell lines with and without 2 µg/ml doxycycline for 48 hours. Statistical significance was determined by unpaired Student's t-test (*p<0.05).

g. Left panel: representative Western blot of endogenous HuD protein from human SH-SY5Y cells stably expressing either the wild type (WT) SOD1 protein or the ALS-associated SOD1(G93A) mutant. Right panel: Quantification of HuD protein levels and statistical analysis of three independent experiments as in FIG. 1A. CPSF73 (Cleavage and polyadenylation specificity factor 73) was used as loading control for the experiments.

h. RT-qPCR analysis of miRNA expression in early symptomatic transgenic SOD1(G93A) mice. Total RNA was extracted from spinal cord of mice at early stage of disease (135 days). rnu1a1 was used as internal control. Data are presented as scatter plot graph of three technical replicates of age-matched non-transgenic controls (n=7) and affected (n=7) spinal cords.

i. Left panel: representative Western blot of endogenous HuD protein from NSC34 cells expressing either the wild type SOD1 protein or the SOD1(G93A) mutant under a doxycycline-inducible promoter. CPSF73 was used as loading control. Right panel: densitometric quantification of HuD protein level. Error bars represent fold change standard deviation derived from three independent experiments. Statistical significance was determined by Paired Student's t-test (***p<0.001).

Figure 4:
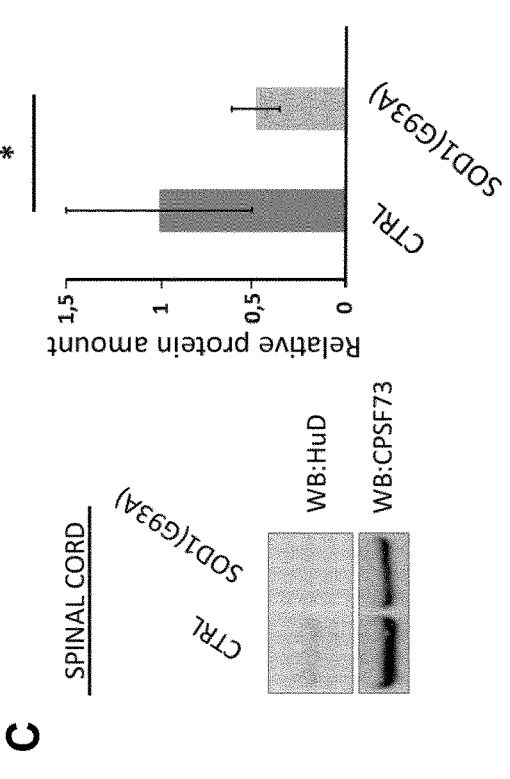
Figure 4:
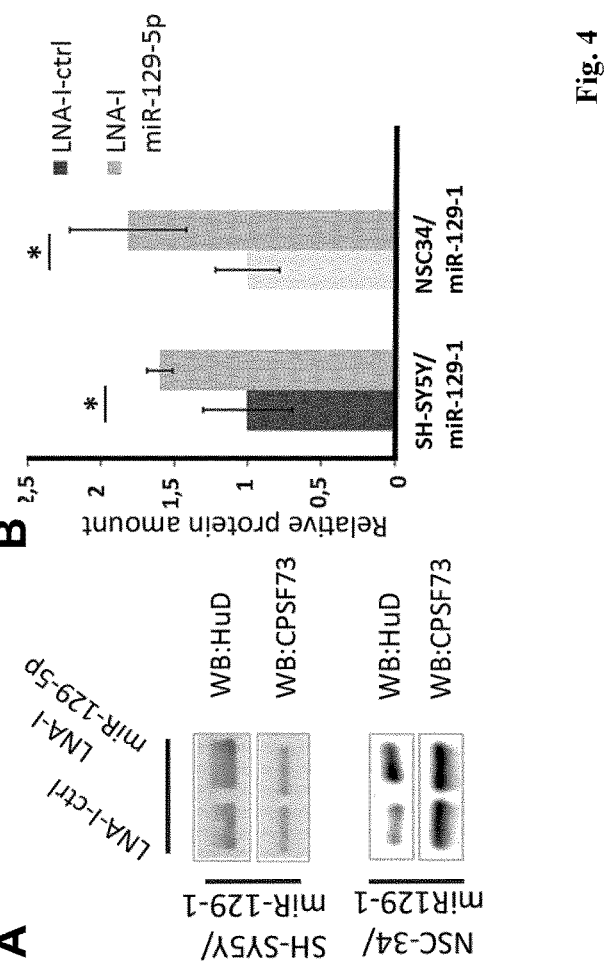

FIG. 4. Antisense inhibition of miR-129-5p restores HuD expression.

a. Representative Western blot Western blot of HuD protein levels in human SH-SY5Y/miR-129-1 and mouse NSC-34/miR-129-1 cells transiently transfected with a scrambled LNA control or a miR-129-5p inhibitor LNA oligonucleotide. CPSF3 was used as loading control.

b. Quantification of HuD protein levels and statistical analysis of three independent experiments. Statistical analysis of three independent experiments as in FIG. 1A.

c. Left panel: representative Western blot of endogenous HuD protein derived from spinal cord of wild type or SOD1(G93A) mutant mice. CPSF73 was used as loading control. Right panel: Quantification and statistical analysis of six independent experiments as in FIG. 1A.

Figure 5:
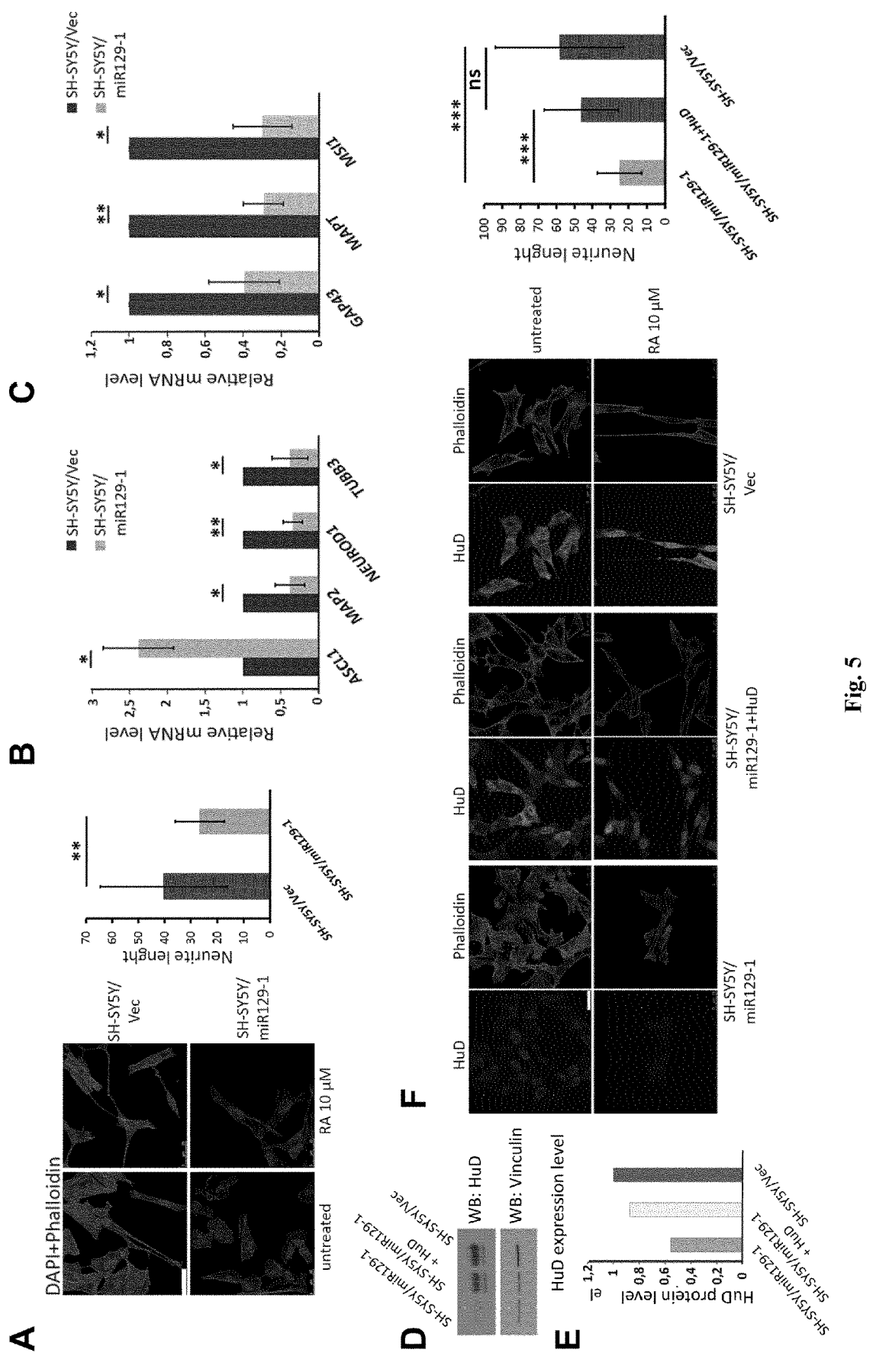

FIG. 5. MiR-129-5p overexpression inhibits neurite outgrowth and differentiation by downregulating HuD.

a. Left panel: Magnification of representative confocal micrographs of control (VEC) and miR-129-5p overexpressing (miR-129) SH-SY5Y cells. Neuronal differentiation was induced by treatment with 10 µM retinoic acid (RA) for eight days and neurites were visualized by phalloidin staining (red). Nuclei were stained with DAPI. Scale bars represent 25 µm. Right panel: Quantification of neurites length after RA-induced differentiation. Average values and standard deviations from three independent experiments are shown. Statistical significance was tested by unpaired Student's t-test, ** denotes p<0.01.

b. Expression of neuronal markers after RA-induced differentiation. Relative mRNA levels of ASCL1, MAP2, NEUROD1, and TUBB3 were measured by RT-qPCR in total RNA purified from SH-SY5Y and in SH-SY5Y/miR-129-1 cells after treatment with 10 µM retinoic acid for eight days. LDH mRNA was used for normalization. Average values and standard deviations from three independent experiments are shown. Statistical significance was tested by unpaired Student's t-test, * denotes p<0.05.

c. Expression of HuD targeted transcripts after RA-induced differentiation. Relative mRNA levels of GAP43, MAPT, and MSI1 were measured by RT-qPCR as in (B). Unpaired Student's t-test; ** denote p<0.01.

d. Western blot analysis of HuD expression of the cell lines described in (f). Vinculin was used as loading control.

e. Densitometric quantification of Western Blot signal showed in FIG. 5d.

f. Left panel: Exogenous expression of a miR-129-5p-resistant HuD cDNA restores neuritogenesis in SH-SY5Y/miR-129-1. Representative confocal micrographs are shown of undifferentiated (untreated) or differentiated (RA 10 µM for eight days) SH-SY5Y transfected either with the empty vector (Vec) or with a plasmid expressing the HuD open reading frame. Cells were stained with phalloidin (red) and anti-HuD antibody (green). Scale bars represent 25 µm for magnified micrographs. Right panel: Quantification and statistical significance was determined with a by paired Student's t-test comparing indicated samples, ***denote p<0.001.

Figure 6:
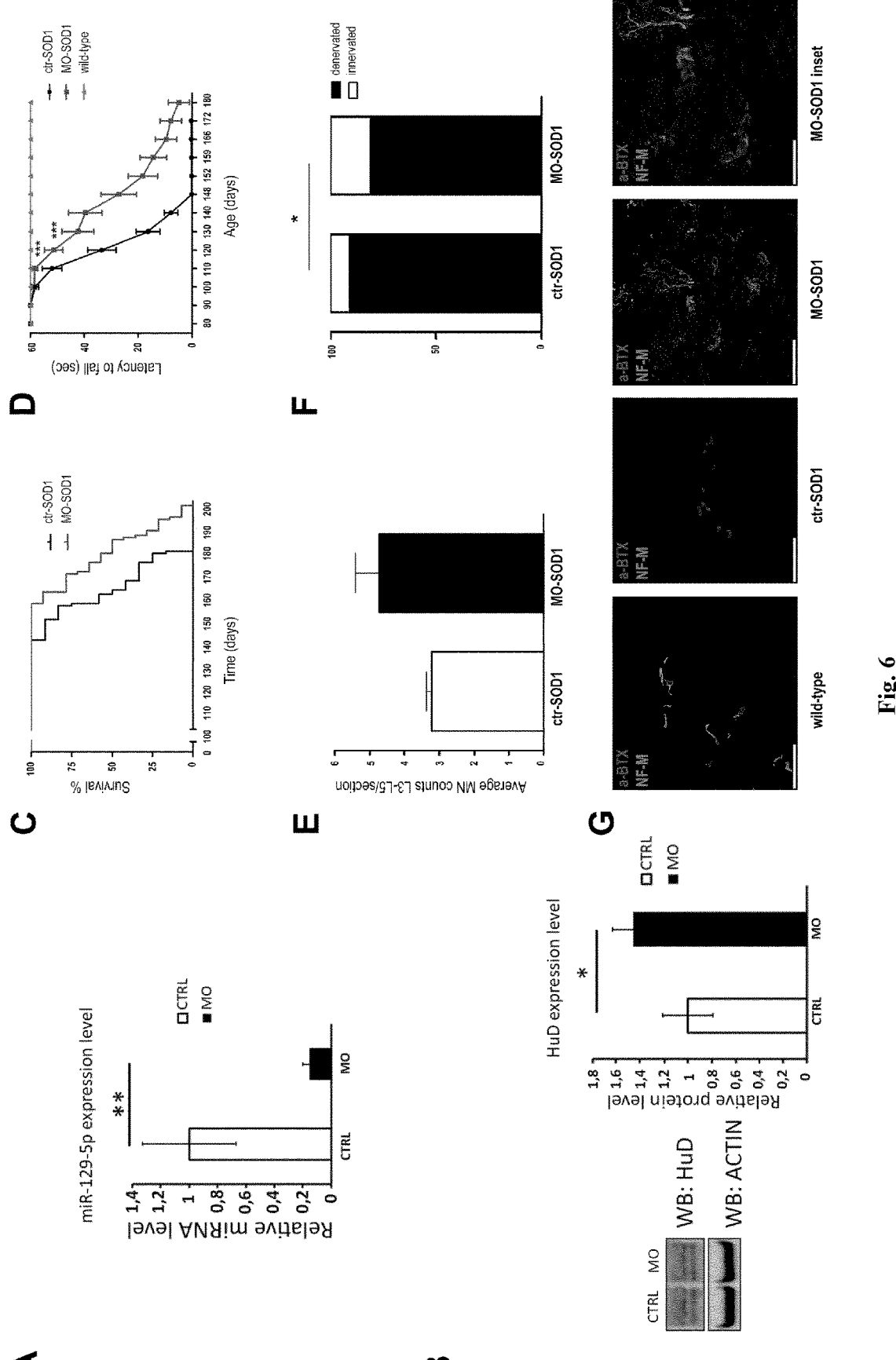

FIG. 6. Morpholino (MO)-miR-129-1 ameliorates pathological phenotype in the SODG93A mouse model.

a. qPCR on 1 week harvested spinal cord of wild-type pups treated intracerobroventricularly with 24 nmoles MO-miR-129 demonstrated a significant decrease of miR-129 expression levels after treatment (4 ctr and 4 MO treated mice, Student's t-test, p<0.01).

b. Western Blot analysis on 1 week harvested spinal cord of wild-type pups treated intracerobroventricularly with 24 nmoles MO-miR-129 detected an increased level of HuD (n=4/groups, Student's t-test, p<0.05).

c. Kaplan-Meier survival curves demonstrated a significantly extended median survival by 22 days in MO-SOD1 mice (n=14) compared to scr-SOD1 animals (n=12) (median survival: MO-SOD1 mice, 180 days, scr-SOD1 mice 160 days; $\chi 2$=7.232, P=0.0072, log rank test).

d. Inverted grid curve data was significantly ameliorated in MO-SOD1 treated mice compared to scr-SOD1 (n=12/group). Data are reported as the mean±SEM for each time point expressed in seconds. ***p<0.001, repeated measures ANOVA with Sidak's post-analysis. Data were analysed up to 130 days, when all animals in each group were still alive.

e. Quantification of motor neurons in the lumbar spinal cords (L3-L5) of MO-SOD1 treated mice and scr-SOD1 mice (mean±SEM). Motor neuron number increased, even if not significantly in the treatment group n=30. Student's t-test, 4 mice/group, p=0.08.

f. Quantification of merged signal showed a significant increase in neuromuscular junction (NMJ) innervation tibial anterior (TA) muscles in MO-SOD1 treated mice (n=4) compared to scr-SOD1 (n=4). *P<0.05, contingency chi-squared test ($\chi 2$=4.153), n=100 NMJs analyzed for each animal.

g. Representative image of NMJ in TA muscles. Axons of presynaptic MNs were stained with antibody raised against neurofilament medium (NF-M) (green). The acetylcholine receptors of the postsynaptic termini were labeled with $\alpha$-bungarotoxin ($\alpha$-BTX; red). The overlay of both signals (yellow) indicates innervation at the motor end-plate. In scr-SOD1 mice, the presynaptic termini present a collapsed structure, suggesting a pathologic NMJ while MO-SOD1 treatment ameliorates NMJ structure and innervation. Scale bar: 75 μm, inset: 50 μm.

Figure 7:

FIG. 7. miR-129-5p expression profile across tissues.

Bar plots of miR-129-5p expression in post-mortem tissues biopsies of two male individuals were derived from the Human miRNA tissue atlas (https colon forward slash forward slash_ccb-web.cs.uni-saarland.de/tissueatlas) (Ludwig, et al., 2016). Shown are raw data, normalized data by quantile normalization and by variance stabilizing normalization (Huber, et al., 2002). The miRNA is highly expressed in brain and spinal cord.

DETAILED DESCRIPTION OF THE INVENTION

Methods

Plasmids and Constructs

The HuD expression construct was obtained from Addgene (pFRT-DestFLAGHA_HuD, Plasmid #65760).

The pre-miR-129 expressing plasmid (miR-129-1 Human MicroRNA Expression Plasmid CAT #: SC400125) and the HOXC10 3'UTR Reporter (Homeo box C10 (HOXC10) (NM_017409) Human 3' UTR CAT #: SC210839) were purchased from Origene.

The CACNG2 and ELAVL4/HuD UTR regions were amplified using the Phusion Hot Start High-Fidelity DNA Polymerase (Finnzymes) according to manufacturer's instructions. The human genomic DNA extracted from HeLa cells was used as the template in the PCR reactions. The sequences of the oligos are indicated in Table 1. The resulting PCR products were purified and cloned into the pGEM® T Easy Vector system (a plasmid vector derived from pUC19, containing T7 and SP6 promoter sequences, a multiple cloning site, and an ampicillin resistance gene, with an approximate size of 3 kilobases, Promega). The insert was verified by nucleotide sequencing.

Cell Lines

Human HEK293T cells (ATCC n. CRL-3216), SH-SY5Y cells (ATCC n. CRL-2266), either un-transfected or stably transfected with cDNAs coding for wild type SOD1 or the mutant SOD1(G93A) (Carri et al, 1997), SH-SY5Y/miR-129-1, SH-SY5Y/Vec, mouse NSC-34/miR-129-1, and NSC-34/Vec (Babetto et al, 2005) were cultured in D-MEM high glucose medium, 10% fetal bovine serum (FBS), 2.5 mM L-glutamine, 100 U/ml penicillin, and 100 μg/ml streptomycin (all products were purchased by Euroclone) at 37° C. with 5% $CO_2$. Stably transfected cells were maintained with 400 μg/ml Gentamycin. NSC-34 stably transfected with the doxycycline-inducible vector for the expression of the SOD1(WT) and the SOD1(G93A) were maintained in F12 (Gibco, Invitrogen), 10% fetal bovine serum (FBS), 2.5 mM L-glutamine, 100 U/ml penicillin, and 100 μg/ml streptomycin at 37° C. with 5% CO2. To induce the expression of transgenic SOD1, NSC-34 cells were treated for 48 h with 2 mg/ml of doxycycline. To induce differentiation of SH-SY5Y cells, the growth medium was exchanged 24 h after seeding for the differentiation medium containing: D-MEM High Glucose medium, 1% FBS, 2.5 mM L-glutamine, 100 U/ml penicillin, and 100 μg/ml streptomycin and 10 μM all-trans retinoic acid. Differentiation medium was replaced every 2 days and the cells grown for up to 6-8 days.

Transfection, DNA Cloning and Luciferase Assays

To generate SH-SY5Y and NSC-34 cells stably expressing the miR-129-1 precursor, transfections were carried out by the classical calcium phosphate procedure. Starting 24 h post transfection cells were maintained in selective medium containing 0.4 mg/ml G418 (Gibco). For the HuD rescue experiments, a construct expressing HuD was transfected by using JetPRIME®-Polyplus-transfection according to the manufacturer's instruction.

MiRCURY LNA-inhibitor transfections were performed by using the Lipofectamine RNAi MAX system (Invitrogen, Paisley, UK) according to protocol. $5 \times 10^4$ cells/well were seeded into 24 multi-well plates, transfected with 75 mM miR-129-5p LNA-inhibitor and collected after 48 and 72 h for SH-SY5Y and NSC34, respectively. The pre-miR-129-1 expressing plasmid pMir and the HOXC10 3'UTR reporter cloned in pMir Target were purchased from Origene. The CACNG2 and ELAVL4/HuD 3' UTR regions were amplified using Phusion Hot Start High-Fidelity DNA Polymerase (Finnzymes) according to manufacturer's instructions. The human genomic DNA extracted from HeLa cells was used as template in the PCR reactions. The sequences of the oligonucleotides used in the PCR reactions are provided in the Table 1.

TABLE 1

| Used oligonucleotides | | |
| --- | --- | --- |
| NAME | SEQUENCE | MIRBASE Accession Number |
| Hsa-miR-30a | ACATC CTCGA CTGGA | MI0000088 |

TABLE 1-continued

TABLE 1-continued

| NAME | SEQUENCE | MIRBASE Accession Number |
|------|----------|--------------------------|
| | AGAA (SEQ ID NO: 4) | |
| Hsa-miR-30b | TGTAA ACATC CTACA CTCAG CTAA (SEQ ID NO: 5) | MI0000441 |
| Hsa-miR-30c | TGTAA ACATC CTACA CTCTC AGCAA (SEQ ID NO: 6) | MI0000254 |
| Hsa-miR-30d | CATCC CCGAC TGGAA GAA (SEQ ID NO: 7) | MI0000255 |
| Hsa-miR-30e | AACAT CCTTG ACTGG AAGAA (SEQ ID NO: 8) | MI0000749 |
| Hsa-miR-29a | CACCA TCTGA AATCG GTTAA (SEQ ID NO: 9) | MI0000087 |
| Hsa-miR-29b | TAGCA CCATT TGAAA TCAGT GTTAA (SEQ ID NO: 10) | MI0000105 |
| Hsa-miR-1 | TGGAA TGTAA AGAAG TATGT ATAA (SEQ ID NO: 11) | MI0000437 |
| Hsa-miR-206 | TGGAA TCTAA GGAAG TGTGT GGAA (SEQ ID NO: 12) | MI0000490 |
| Hsas-miR-15a | GCAGC ACATA ATGGT TTGTG AAA (SEQ ID NO: 13) | MI0000069 |

| NAME | SEQUENCE | MIRBASE Accession Number |
|------|----------|--------------------------|
| Hsa-miR-15b | GCAGC ACATC ATGGT TTACA AA (SEQ ID NO: 14) | MI0000438 |
| Hsa-miR-16 | CAGCA CGTAA ATATT GGCGA A (SEQ ID NO: 15) | MI0000070 |
| Hsa-miR-195 | TAGCA GCACA GAAAT ATTGG CAA (SEQ ID NO: 16) | MI0000489 |
| Hsa-miR-203 | GTGAA ATGTT TAGGA CCACT AGAAA (SEQ ID NO: 17) | MI0000283 |
| Hsa-miR-9 | TCTTT GGTTA TCTAG CTGTA TGAAA (SEQ ID NO: 18) | MI0000466 |
| Hsa-miR-455-3p | GCAGT CCATG GGCAT ATTCA CAA (SEQ ID NO: 19) | MI0003513 |
| Hsa-miR-124 | CACGC GGTGA ATGCC AAA (SEQ ID NO: 20) | MI0000443 |
| Hsa-miR-125a-3p | GTGAG GTTCT TGGGA GCCAA A (SEQ ID NO: 21) | MI0000469 |
| Hsa-miR-125a-5p | CTGAG ACCCT TTAAC CTGTG AAA (SEQ ID NO: 22) | MI0000469 |

TABLE 1-continued

Used oligonucleotides

| NAME | SEQUENCE | MIRBASE Accession Number |
|------|----------|--------------------------|
| Hsa-miR-125b | CCCTG AGACC CTAAC TTGTG AAA (SEQ ID NO: 23) | MI0000446 |
| Hsa-miR-132 | CAGTC TACAG CCATG GTCGA AA (SEQ ID NO: 24) | MI0000449 |
| Hsa-miR-17 | GTGCT TACAG TGCAG GTAGA (SEQ ID NO: 25) | MI0000071 |
| Hsa-miR-7 | TGGAA GACTA GTGAT TTTGT TGTAA A (SEQ ID NO: 26) | MI0000263 |
| Hsa-miR-200c | TAATA CTGCC GGGTA ATGAT GGAAA A (SEQ ID NO: 27) | MI0000650 |
| Hsa-miR-885-3p | AGGCA GCGGG GTGTA GTGGA TAAA (SEQ ID NO: 28) | MI0005560 |
| Hsa-miR-455-5p | TATGT CCTTT GGACT ACATC GAAA (SEQ ID NO: 29) | MI0003513 |
| Hsa-miR-1179 | AAGCA TTCTT TCATT GGTTG GAAA (SEQ ID NO: 30) | MI0006272 |
| Hsa-miR-1287 | TGGAT CAGTG GTTCG AGTCA AA (SEQ ID NO: 31) | MI0006349 |

TABLE 1-continued

Used oligonucleotides

| NAME | SEQUENCE | MIRBASE Accession Number |
|------|----------|--------------------------|
| Hsa-miR-129-5p | CUUUU UGCGG UCUGG GCUUG C (SEQ ID NO: 2) | MIMAT0000242 |
| SnoRD25 | GATGA GGACC TTTTC ACAGA CCTG (SEQ ID NO: 32) | Gene ID: 9303 |
| Cloning Primers | | |
| CACNG2 UTR FW | TCCAC TCCAA CACAG CCAAC (SEQ ID NO: 33) | |
| CACNG2 UTR REV | CTTAC GCGTT TGTTT TCTTC TTCCC TCGTT TA (SEQ ID NO: 34) | |
| HUD UTR FW | CCAAA CAAAG CCCAC AAGTC CTGA (SEQ ID NO: 35) | |
| HUD UTR REV | ATTAC GCGTA TGTCA TCAGG TATCC CCCT (SEQ ID NO: 36) | |

PCR products were purified, cloned into the pGEM® T Easy (Promega) and sequenced. The HuD plasmid was purchased form Addgene (Plasmid #65760).

For luciferase assays, $1.5 \times 10^5$ HEK293T cells/well were seeded in a 24-multiwell, and plasmids were transfected the following day using polyethylenimine (PEI, Sigma) according to the manufacturer's instruction. A constant amount of pRL-TK (Promega) was cotransfected with the pMiR, and the construct containing the specific 3' UTR fragment downstream of the Firefly luciferase ORF. 24 h after transfection, cells were lysed in 100 µg/well of the passive lysis buffer 1× according to manufacturer's instructions. To obtain a complete lysis, the cells were subjected to freeze-thawing. The luciferase assays were carried out using the DUAL-LU-CIFERASE® Reporter Assay System (a dual reporter enzyme system comprising firefly luciferase from Photinus pyralis and Renilla luciferase from *Renilla reniformis*, utilizing D-luciferin and coelenterazine as respective substrates, Promega) and a BERTHOLD LUMINOMETER (Berthold Inc.)

Animals

Transgenic mice expressing the human SOD1 gene with the G93A mutation (strain B6.Cg-Tg(Sod1-G93A)1Gur (Gurney et al, 1994), were originally purchased from the Jackson Laboratory (Bar Harbor, ME) and maintained on C57BL/6J strain colony at the Mario Negri Institute in compliance with institutional guidelines that comply with national (Legislative Degree 26, March 2014) and international (EEC Council Directive 2010/63, August, 2013) laws and policies. The experiments were planned and conducted with the aim of minimizing the number of sacrificed animals. Transgenic female mice were killed at 10, 15, and 22 weeks of age, corresponding to pre-symptomatic onset, early symptomatic, and end-stage of the disease, respectively. Non-transgenic age-matched littermates were used as controls. RNA extraction was made from the frozen lumbar spinal cord using ReliaPrep RNA Tissue Miniprep System (Promega). Procedures involving animals and their care were conducted in conformity with institutional guidelines that comply with national (Legislative Degree 26, March, 2014) and international (EEC Council Directive 2010/63, August, 2013) laws and policies. Animals studies were approved by the Mario Negri Institute Animal Care and Use Committee and by the Italian Ministerial decree no. 84-2013.

Patient Information

All procedures involving human participants were in accordance with the ethical standards of the institutional ethics committee and with the 1964 Helsinki declaration and its later amendments. Ethical approval was obtained from the local committee (University of Milano-Bicocca, Italy; protocol MyoSLA 30 Mar. 2015). 27 patients affected by sporadic ALS (sALS) diagnosed according to El Escorial criteria (Brooks et al, 2000) were consecutively recruited at the NEMO center (Milano, Italy) following informed consent. ALS patients negative for SOD1, TARDBP, FUS mutations and for C90RF72 hexanucleotide repeats expansions were considered eligible for the study. See Table 2 for demographic and clinical characteristics. ALSFRS-R scores were recorded together with the disease progression index (DPI), defined as: [(48-ALSFRS-R score at recruitment)/disease duration in months](Tremolizzo et al, 2013). 25 healthy subjects, age- and sex-matched to sALS patients, were recruited. PBMC samples were available from 8 patients affected by Alzheimer's Disease recruited at the S. Gerardo Hospital (Monza, Italy) and diagnosed according to the NINCDS-ADRDA criteria (McKhann et al. 1984). For each patient Mini-Mental State Examination (MMSE) score was collected. Samples from 8 age- and sex-matched controls (MMSE≥26) were also analyzed. Exclusion criteria for all the recruited subjects were considered cancer, autoimmune and inflammatory diseases. Moreover, healthy controls were not affected by any neurological or psychiatric condition, nor were they taking psychoactive drugs.

TABLE 2

Clinical and demographic data of the recruited subjects. ALSFRS-R, ALS functional rating scale-revised version; DPI, disease progression index; n.a., not applicable; NIV, non-invasive ventilation; PEG, percutaneous endoscopic gastrostomy; *50 mg bid.

| | CTRL n = 25 | sALS n = 27 |
|---|---|---|
| Sex, M/F | 12/13 | 12/15 |
| Age, years | 6.8 ± 11.7 (38-78) | 62.7 ± 12.1 (41-78) |
| Duration, months | n.a. | 29.8 ± 27.7 (0-102) |
| Onset, Bulbar/Spinal | n.a. | 8/19 |
| ALSFRS-R | n.a. | 22.2 ± 7.3 (5-37) |
| DPI | n.a. | 0.82 ± 0.51 (0.17-1.77) |
| PEG, yes/no | n.a | 7/20 |
| NIV, yes/no | n.a. | 8/19 |
| Riluzole, yes/no* | n.a. | 26/1 |

PBMCs Isolation

Peripheral blood samples (15 ml) were drawn from each subject (ALS and AD) in tubes containing $K_2$EDTA after overnight fasting. PBMCs were collected as previously described (Arosio et al, 2016). Briefly, whole blood samples were diluted with the same amount of saline solution layered on Ficoll-Histopaque (GE Healthcare) and centrifuged for 30 min at 490×g at RT. PBMCs were collected from the interface between plasma and Ficoll-Histopaque, washed with saline solution, aliquoted and stored at −80° C.

RNA High Throughput Sequencing

Four biological replicates of SH-SY5Y cells (ATCC n. CRL-2266), SH-SY5Y/SOD1, of SH-SY5Y/SOD1(G93A) cells (Carri et al, 1997), four biological replicates, were sequenced by whole-genome small RNA deep-sequencing (sRNAseq). In brief, total RNA was extracted using TRIzol™ (a monophasic solution containing phenol and guanidinium thiocyanate, Invitrogen) according to the manufacturer's instructions. Samples were enriched for small RNAs up to 200 bp by size selection using PURE-LINK™ miRNA Isolation Kit (an miRNA isolation kit comprising silica-based purification columns, lysis buffer, wash buffers, and elution buffer specifically designed for the isolation and purification of microRNA from biological samples, LifeTech). RNA purity, integrity and size distribution were assessed using an Agilent 2100 Bioanalyzer (Agilent Technologies). Enriched RNA samples were processed using the Small RNA Expression Kit according to the manufacturer's protocol (Small RNA expression kit, rev. C, Applied Biosystems). RNA was first hybridized and ligated with the adapter mix "A", subsequently reverse transcribed and treated with RNAse H. The obtained cDNA libraries were PCR amplified, purified and size-selected by PAGE, resulting in libraries containing inserted small RNA sequences of 20-40 bp length. Size, integrity and purity of the libraries were verified by the Agilent 2100 Bioanalyzer (Agilent Technologies). cDNA libraries were barcoded using the Solid RNA barcoding kit and amplified onto beads using emulsion PCR. Templated beads were deposited on slides and analysed using the Applied Biosystems SOLID™ 4 platform (Applied Biosystems). The quality filtered reads were trimmed to 25 nts. Filtered reads were mapped against all annotated human precursors miRNA sequences (miR-Base v19.0) (Griffiths-Jones S et al, 2008) using SHRiMP 2.0.1 (Rumble et al, 2009). Mature miRNAs were extracted and reformatted with custom R scripts from the SHRIMP output. Differential expression analysis was performed with the edgeR Bioconductor statistical library (Robinson et al, 2010) version 3.0.8 on R version 2.15.3.

RNA Extraction and Quantitative Real-Time PCR Assay (qPCRs)

The protocols for mRNA, pri-, pre-, and mature miRNA extraction, for retrotranscription, and for the qPCR assays are provided below. The sequences of the oligonucleotide primers are listed in the Table 1 above.

Protein Extracts and Immunoblotting

Human HEK293T cells (ATCC n. CRL-3216), SH-SY5Y cells (ATCC n. CRL-2266), either un-transfected or stably transfected with cDNAs coding for wild type SOD1 or the mutant SOD1(G93A) (Carri et al, 1997), SH-SY5Y/miR-129-1, SH-SY5Y/Vec, mouse NSC-34/miR-129-1, and NSC-34/Vec (Babetto et al, 2005) were washed once in PBS 1× (Euroclone) and then lysed in 0.5 ml of cold Lysis Buffer (Tris HCl 50 mM pH 7.5, NaCl 150 mM, 1% NP40, 5 mM EGTA) with protease inhibitors (Roche). The samples were incubated on ice for 20 min, centrifuged at 15000 rcf for 15 min at 4° C., and the supernatant were collected. An aliquot of the cell lysate was used for protein quantification. Protein were resolved by 7% or 10% SDS-PAGE, transferred to nitrocellulose membranes (Whatman GmbH) in normal Transfer Buffer (25 mM Tris, 192 mM Glicine, 20% Methanol) at 100 Volts for 2 h or in High Molecular Weight protein (25 mN Tris, 192 mM Glicine, 10& Methanol and 0.1% SDS) at 15 Volts overnight. Membrane were blocked using 5% non fat dried milk in PBST (0.1% (v/v) Tween 20 in 1×PBS) and incubated with the respective antibodies overnight at 4° C. Primary antibodies used for detection are listed in the Antibodies section.

After washing, membranes were incubated with peroxidase-conjugated secondary antibody anti-mouse IgG (Cell signaling, 1:5000 dilution) or anti-rabbit IgG (Cell signaling 1:5000 dilution), in PBST with 5% non fat dried milk for 1 h at room temperature. After washing as above, the chemoluminescent signals developed by ECL reagents (Millipore) were detected using films. Exclusively the western blot in FIG. 2F was run on a precast polyacrylamide gel (4-12%) (Invitrogen), transferred using a semi-dry system and acquired using the LI-COR Biosciences technology, Odissey FC. In particular, secondary anti-mouse IR-DYE 800 CW (1:20000) and anti-rabbit IR-DYE 680 RD (1:20000) were added for 1-hour RT.

Immunofluorescence

SH-SY5Y cells were grown on glass coverslips were fixed with 4% PFA for 20 min and permeabilized with 0.2% Triton X-100 for 5 min. After blocking with FBS 20% in PBS with 0.05% Tween for 1h, coverslips were incubated overnight at 4° C. with Alex Fluor phalloidin-488 (Fisher Scientific) in PBS containing 0.2% BSA. 24 h later, coverslips were washed with PBS with 0.2% BSA, incubated with anti-HuD antibody (SC48421, 1:200 dilution) for 1 h at RT. After washing, the slides were first incubated with anti-mouse Alexa Fluor 647 antibody (Cell signaling), and then stained for 10 min at RT with 1 μg/ml 4,6-diamidino-2-phenylindole (DAPI, Sigma. The fluorescence 12-bit images were collected with a Leica TCS SP2 AOBS confocal microscope with the 63× oil immersion objective.

Morpholino (MO) Treatment

The MO sequence targeting miR-129-1 and/or miR-129-5p was ACAGCAAGCCCAGACCGCAAAAAGA (SEQ ID NO: 3) and was synthesized without any modifications by Gene Tools Laboratories. The scr-MO sequences were designed based on the best control sequence predicted by the bioinformatic tool (Gene tools, www dot gene-tools dot com). The ctr-MO was a standard control oligo with Morpholino chemistry provided by Gene Tools, sequence: CCT CTT ACC TCA GTT ACA ATT TAT A (SEQ ID NO: 39, Gene tools, www dot gene-tools dot come). MOs were dissolved in sterile saline solution at the appropriate concentration for in vivo experiments. All animal experiments were approved by the University of Milan and Italian Ministry of Health review boards, in compliance with US National Institutes of Health Guidelines. Adult SOD1 mice, expressing human sod1 gene with the g93a mutation, were injected with MO (40 nMoles) at early symptomatic phase (at P80) with ICV injection follow the standard stereotactic coordinate.

Pathological ALS Phenotype Analysis after MO Treatment Neuromuscular Evaluation and Survival All groups of SOD1 mice were monitored daily after treatment with MOs sequence or scr for phenotypic hallmarks of disease. The investigators that executed the functional assessment were blind to the treatment. Motor function was tested weekly with hand inverted grid test (Nizzardo et al., 2016). The animals were sacrificed when they were unable to right themselves within 30 s when positioned in a supine position.

In Vivo Motor Neuron (MN) and Neuromuscular Junction (NMJ) Count

Lumbar spinal cord and tibial anterior (TA) muscles were collected at P120 and used for histopathological analysis (n=4/group). Serial cross sections (20 μm thick) of the lumbar spinal cords (L1-L5) were made and stained with the specific MN marker with goat polyclonal anti-Choline Acetyl Transferase (ChAT) antibody (Millipore, 1:125, secondary antibody, Alexa 594). The number of all MNs counted in these cross sections were analyzed. The sections were analyzed at 20× magnification in the ventral horn (either left or right) for the presence of all stained MNs in that region. TA were cryosectioned (20 μm) and stained for NMJ detection and count. All sections were saturated with 10% bovine serum albumin and 0.3% Triton X-100 for 1 h at room temperature before incubation with rabbit Neurofilament Medium (NF-M, Millipore 1:250) overnight at 4° C. The next day, the slides were incubated with Alexa Fluor 488 (1:1000; Life Technologies) and α-bungarotoxin 555 (1:500, Life Technologies). A minimum of 100 NMJs from each muscle were randomly selected and the number of denervated/degenerated NMJs was determined for each muscle group in each animal based on NF-M/α-BTX staining.

Statistical Analysis

All statistical analyses were performed with Excel and GraphPad Prism. When making multiple comparisons on a single data set one-way analysis of variance (ANOVA) was used and when several variables were taken into account, two-way ANOVA was used, followed by appropriate post hoc analysis. Two-tailed, unpaired Student's t test was used to compare two groups. Kaplan-Meier survival analysis and the log-rank test were used for survival comparisons while contingency chi-square test was applied to NMJ count. The data met the assumptions of the specific statistical tests chosen, and *P≤0.05; P≤0.01; *P≤0.001 were considered significant. All experiments were performed in triplicate at a minimum. Individual statistical tests are detailed in the figure legends. All results are expressed as mean±SEM or mean±SD. Western blot images were analyzed using the ImageJ software (Schneider et al, 2012). The value of each band was normalized to the intensity of the corresponding housekeeping band, thus obtaining relative intensity values. In the qPCR experiments, for relative quantification of each target vs. housekeeping mRNA, the comparative CT method was used as previously described (Sala et al, 2010).

mRNA Extraction, Reverse-Transcription and qPCRs Assays

RNAs were extracted using TRIzol™ Reagent (Thermo Fisher Scientific) and subsequently purified using silica membrane spin columns from RNeasy Mini Kit (Qiagen). RNA quantity and purity were assessed using a NanoDrop (Thermo Fisher Scientific Inc.). 2 □g of total RNA were reverse-transcribed using the random hexamers-based High Capacity cDNA Reverse-Transcription Kit (Applied Biosystem), according to manufacturer's instructions. Gene expression of differentiation markers was measured by qPCR with SYBR Green qPCR master mix (Applied Biosystem). The primer sequences are provided in Table 1. Normalization of cDNA loading was obtained running all samples in parallel using human LDH as housekeeping gene. The amplification protocol was as follow: denaturation and activation at 95° C. for 10 min, followed by 40 cycles at 95° C. for 15 s, 60° C. for 1 min and 95° C. for 15 s.

miRNA Extraction, Reverse Transcription and qPCR Assays

Cell pellets were lysed using TRIzol™ (Thermo Fisher Scientific) and miRNAs were extracted using miRCURY™ RNA Isolation Kit—Cell and Plant (Exiqon) according to manufacturer's instructions. RNA concentration was determined spectrophotometrically at 260 nm and each RNA sample was loaded on 2% agarose gel to evaluate RNA quality. To assess pri-miRNA levels, RNA (2,000 ng) was reverse transcribed using High Capacity RNA-to-cDNA Kit (Applied Biosystems) according to manufacturer's instructions. For the analysis of pri-miRNA levels, cDNAs A were amplified in triplicate in the ABI Prism 7500 HTSequence Detection System (Applied Biosystems) using TaqMan® Pri-miRNA Assays (Applied Biosystems, pri-miR-129-1 assay ID: Hs03302824; pri-miR-141 assay ID: Hs03303157; pri-miR-3529 assay ID: Hs03302865; beta-actin assay ID: Hs99999903_ml).

To assess pre-miRNA levels, RNA (500 ng) was reverse transcribed using miScript II RT Kit (Qiagen) according to manufacturer's instructions. For the analysis of pre-miRNA levels, cDNAs obtained from 20 ng RNA were amplified in triplicate in the ABI Prism 7500 HTSequence Detection System (Applied Biosystems) using miScript Precursor Assays (Qiagen, pre-miR-7-1 assay ID: MP00003500; pre-miR-129-1 assay ID: MP00000658; pre-miR-129-2 assay ID: MP00000672; pre-miR-200c assay ID: MP00001414; GAPDH F: TCTTTTGCGTCGCCAG (SEQ ID NO: 37); GAPDH R: CCCGTTCTCAGCCTTGACGGTG (SEQ ID NO: 38)).

For relative quantification of each target vs. ACTIN or GAPDH mRNA, the comparative CT method was used as previously described (Sala, et al., 2010).

To assess miRNA levels, reverse transcription was carried out on 2 µg of total RNA using All-In-One miRNA qRT-PCR kit (Genecopoeia), according to the manufacturer's instructions or according to (Reber, et al., 2016). Briefly, in the reverse transcription reaction a poly-A tail was added to the mature microRNA template by *E. coli* Poly(A) polymerase (New England Biolabs). The cDNA was synthesized by the Affinityscript polymerase (Agilent Technologies), using a poly-T primer with a 5' universal tags and a 3' a degenerate anchor. The cDNA template was then amplified using a miRNA-specific forward primer and a universal reverse primer complementary to the universal tag. SYBR Green (MESA GREEN qPCR MasterMix Plus, Eurogentec) or All-In-One qPCR-Mix (Genecopoeia) was used for detection. MiRNA levels of SHSY-5Y cells were measured as biological or technical replicates and were normalized to SnoRD25. PMBC miRNA expression levels were normalized to miR-16 and SNORD25 expression level.

Reverse Transcription and qPCR for RNA Extracted from Spinal Cord of ALS Mice.

5 ng of template RNAs were reverse transcribed and amplified using the miRCURY LNA™ Universal RT microRNA PCR (Exiqon) according to manufacturer's instructions. Quantitative PCR was performed on a customized Pick & Mix PCR panels that consist of 96-well PCR plates containing a selection of dried down microRNA LNA™ PCR primer sets. MiRNAs were normalized on rnu1a1.

Antibodies

In this study the following antibodies were used: rabbit polyclonal anti Hoxc10 (AVIVA ARP39274_P050 1:1,000 dilution); rabbit polyclonal anti-CACNG2 (AVIVA ARP35189_050 1:1,000 dilution); mouse monoclonal anti-HuD (SC48421, 1:2,000 dilution); goat polyclonal anti-LDH (Abcam 1222 1:1,000 dilution); goat polyclonal anti-Drosha (Santa Cruz Biotechnology, sc31159, 1:500 dilution); mouse monoclonal anti-Dicer (Santa Cruz Biotechnology, sc136980 1:500 dilution); rabbit polyclonal anti-TAF15 (Bethyl A300-308 1:1,000 dilution); rabbit polyclonal anti-EWS (Bethyl A300-418 1:1,000 dilution); mouse monoclonal-TDP43 (Santa Cruz Biotechnology, sc100871 1:1,000 dilution); rabbit polyclonal anti-FUS (homemade 1:5,000 dilution); rabbit polyclonal anti-Exportin 5 (Santa Cruz Biotechnology, sc-66885 1:5000 dilution); rabbit polyclonal anti-CPSF73 (1:5,000 dilution, (Jenny, et al., 1996)). All the antibodies were diluted in PBS-Tween 0.01%, milk 5%.

Analysis of Neurite Outgrowth

Neurite length measurement was obtained on RA-differentiated SH-SY5Y cells transfected either with empty vector, or miR-129-1 or miR-129-1 and HuD ORF lacking the miR-129-1 binding site by manually tracing the longest neurite per cell (using Image J software) for all cells in a field that had an identifiable neurite. Length were determined as the distance between the edge of nucleus and the tip of the growth cone. Photographic images were taken at least from three random fields per each cover slip from three biological replicates. The analyses were carried out "blind" to avoid any subjective influences during the measurements. Data represent mean±SD; ***P<0.001 (Lestanova et al., 2016).

EXAMPLES

Example 1: MiR-129-5p is Up-Regulated in Human and Mouse Models of SOD1-Linked ALS and in PBMCs of Sporadic ALS Patients To determine whether the expression of components of the miRNA processing apparatus and of miRNAs was influenced by a pathogenic SOD1 mutation the inventors first compared the abundance of components of the miRNA biogenesis machinery between human neuroblastoma SH-SY5Y cells stably expressing either the wild type SOD1 (SH-SY5Y/SOD1 cells) or the mutant SOD1(G93A) protein (SH-SY5Y/SOD1(G93A) cells (Carri et al, 1997) (FIGS. 1*a* and *b*). Western blot analysis showed a significant downregulation of DROSHA and of its cofactor DGCR8, which process pri-miRNA into pre-miRNA, in SOD1(G93A) cells compared to cells expressing the wild type SOD1 protein (FIG. 1*a*). Intriguingly, the inventors also found a 2- to 3-fold increase in the expression of DICER, the RNase III enzyme that processes pre-miRNA to mature miRNA in the cytosol (FIG. 1a). Since, the expression of DROSHA was shown to be negatively regulated by the protein EWSR1 (Ewing Sarcoma RNA binding protein 1) (Tremolizzo et al, 2013), the inventors also analyzed EWSR1, FUS and TDP-43 protein levels in SOD1(G93A) cells (FIG. 1b). While, neither TDP-43 nor FUS levels changed, the inventors found a strong upregulation of the EWSR1 RNA binding protein, which is consistent with the observed downregulation of DROSHA.

Overall, the present results indicate that expression of the mutant SOD1(G93A) protein affects the abundance of components of the miRNA processing machinery suggesting that the miRNA transcriptome might also be altered in SOD1 (G93A) cells.

To test this hypothesis, the inventors performed high-throughput sequencing on the small RNA fraction (miRNAseq) of SH-SY5Y/SOD1 and SH-SY5Y/SOD1(G93A) cells identifying nine differentially expressed miRNAs (Table 3).

TABLE 3

| Differentially expressed miRNAs in SH-SY5Y/SOD1(G93A) cells. | | |
|---|---|---|
| ENSEMBL ID | MiR | Log2 FC |
| ENSG0000199077 | hsa-mir-129-2 | UP mt |
| ENSG0000207598 | hsa-mir-124-3 | DW mt |
| ENSG0000207705 | hsa-mir-129-1 | UP mt |
| ENSG0000207703 | hsa-mir-7-2 | UP mt |
| ENSG0000207713 | hsa-mir-200c | UP mt |
| ENSG0000221419 | hsa-mir-1287 | UP mt |
| ENSG0000221630 | hsa-mir-1179 | UP mt |
| ENSG0000216135 | hsa-mir-885 | DW mt |
| ENSG0000207726 | hsa-mir-455 | DW mt |

In addition, the inventors used the T-REX algorithm (from Targets' Reverse Expression, (Volinia et al, 2010)) to predict additional miRNAs affected by the expression of the mutant SOD1 protein based on previous microarray profiling of SH-SY5Y/SOD1 and SH-SY5Y/SOD1(G93A) cells (Lenzken et al, 2011). Based on the results of these two approaches the inventors compiled a panel of 27 miRNAs that were validated by quantitative real-time RT-PCR (qRT-PCR, FIG. 1c). The inventors identified four significantly downregulated miRNAs (miR-29b, miR-30c, miR-30-e, and miR-124) and three significantly upregulated miRNA (miR-29a, miR-129-5p, and miR200c), miR-455 is also upregulated. Interestingly, the most downregulated miRNA, miR-124 (0.2 fold change) plays a well-described role in neuronal differentiation (Sun et al, 2013).

To determine if the effect of the expression of the mutant SOD1 protein on the miRNA transcriptome was also occurring in vivo and to identify consistently affected miRNAs, the inventors selected a panel of 20 of the 27 miRNAs for further analysis in the spinal cord of a SOD1 (G93A) mouse model based on their known implication in neuronal and neurodegenerative pathways. While the expression of the majority of the analysed miRNAs was either unchanged or not significantly affected at the pre-onset (10 weeks), and at symptomatic stage (22 weeks) of the disease (FIG. 2a), miR-129-5p and miR-200c were up-regulated at the early symptomatic stage (15 weeks, FIG. 2a). Consistent with the report of Williams et al. (Williams et al, 2009), the inventors also found an upregulation of miR-206 throughout all the stages examined. Based on these results, the inventors decided to increase the subset of mice at this stage of disease in which to measure the expression of miR-129-5p and miR-200c, and miR-30c as a control miRNA whose level was not affected by the mutation. While the up-regulation of miR-129-5p was confirmed, the expression of miR-200c could be detected in only three of the seven samples that were analyzed (FIG. 2b).

MiRNAs circulating in the blood, either in cell-free plasma or in PBMCs, are currently under evaluation as potential biomarkers not only in cancer but also in neuro-degenerative pathologies. Thus, the inventors analysed the expression of the conserved miRNAs in PBMCs obtained from a small group of sporadic ALS patients. Although of the 20 miRNAs analysed only seven could be detected and reliably quantified in these PBMC samples, these analyses confirmed the upregulation of miR-129-5p and miR200c (FIG. 2c). The inventors therefore measured miR-129-5p and miR-200c levels, along with miR-30c as negative control, in a larger cohort of sporadic patients (Table 2) and found that miR-129-5p was on average increased by two-fold (p<0.001, t test) and miR-200c by almost three-fold (p<0.001, z test) in sporadic ALS patients when compared to controls (FIG. 2d). No influence of demographic and clinical characteristics of recruited subjects was evidenced on all investigated parameters. No significant difference was found in all evaluated parameters by dichotomizing ALS patients based on site of onset, presence of percutaneous endoscopic gastrostomy (PEG) or non-invasive ventilation (NIV), and riluzole treatment. Of note, the inventors confirmed a significant increased expression of miR-129-5p and miR-200c also in PBMC samples from Alzheimer's disease subjects compared with controls. miR-30c level, specifically for this disease, showed also a significant increase (FIG. 2e).

Overall, the analysis of miRNA expression in in vitro and in vivo models of SOD1(G93A)-linked ALS and in sporadic ALS patients revealed an association between a higher abundance of specific miRNAs and ALS pathogenesis, suggesting the presence of a common mechanism underlying the disease. Since miR-129-5p showed the strongest upregulation and the smallest dispersion in all disease paradigms the inventors focused on this miRNA for the identification of its putative target genes and the characterization of the role they it may play in ALS onset and progression.

Example 2: Overexpression of miR-129-1 Inhibits Neurite Outgrowth and Differentiation Via HuD Silencing The inventors used the prediction algorithm DIANA-microT to identify ALS-related potential target genes for miR-129-5p. Among the top-ranking putative targets, the inventors selected CAGN2, ELAVL4/HuD, and HOXC10 for experimental validation. CACNG2 (Calcium channel, voltage-dependent, gamma subunit 2), also known as star-gazin, is involved in the transport of AMPA receptors to the synaptic membrane, and the regulation of their receptor rate constant (Chen et al, 2000). ELAVL4/HuD plays well-characterized role in neuronal cell identity, maturation and survival (Bronicki & Jasmin, 2013). Interestingly, adult HuD-deficient mice exhibit an abnormal hind limb reflex and poor rotarod performance (Akamatsu et al, 2005). HOXC10 belongs to the homeobox family of transcription factors and is involved in motor neuron differentiation (Wu et al, 2008).

To identify target genes of miR-129-5p the inventors generated human neuroblastoma SH-SY5Y cells and mouse motoneuron like NSC-34 cells stably expressing the precursor miR-129-1 (SH-SY5Y/miR-129-1 and NSC-34/miR-129-1, respectively, FIG. 3a). These cell lines were used to investigate whether CAGN2, ELAVL4/HuD, and HOXC10 can be directly targeted by miR-129-5p. To this end, the inventors generated luciferase reporter constructs containing the 3' UTR of the human genes. After transfection of the reporters into HEK293 cells stably expressing the precursor miR-129-1, a significant repression of luciferase activity was observed for all 3'UTR reporters (FIG. 3b). The inventors further examined if miR-129-5p repressed the level of the endogenous CACNG2, ELAVL4/HuD, and HOXC10 proteins in SH-SY5Y/miR129-1 (FIG. 3c). Western blot analysis showed a strong reduction of HuD expression, while CACNG2 protein level was only slightly diminished. In contrast, the inventors observed increased expression of HOXC10. These observations suggest that only the ELAVL4/HuD gene is a bona-fide target of miR129-5p. This conclusion is confirmed by the analysis of the endogenous HuD levels in NSC-34/miR-129-1 cells where a decrease of HuD protein by ~40% was observed (FIG. 3d). Moreover, the inventors mutated the miR-129-5p binding site in the HuD 3'-UTR and performed a luciferase reporter assay observing that miR-129-5p did not affect luciferase activity controlled by mutant HuD UTR (FIG. 3e).

The inventors further analysed the endogenous HuD expression in SH-SY5Y/SOD1(G93A) cells and in brain of SOD1(G93A) mice at the early stage of disease (that have increased expression of miR-129-5p, FIG. 2a) observing in both paradigms a specific reduction of HuD expression (FIGS. 3g and 3h, respectively). An even stronger reduction of HuD expression was observed in an inducible system of NSC-34 cells engineered to express either human SOD1 wild-type or the (G93A) mutant protein upon doxycycline treatment (Prell et al, 2012) (FIG. 3i), consistent with a two-fold increase of miR-129-5p (p<0.05) in the NSC-34/SOD1(G93A) cells (FIG. 3f).

Since overexpression of miRNAs can downregulate mRNAs that under physiological conditions would not be affected, the inventors also performed the reverse experiment and tested if depletion of miR-129-5p leads to an increase in HuD protein. To this end, the inventors transfected either a scrambled, or a miR-129-5p locked nucleic acid (LNA) oligonucleotide inhibitor in SH-SY5Y/miR-129-1 and NSC-34/miR-129-1 cells to bind and sequester the free miRNA. As shown in FIG. 4a,b, in both cell lines LNA-mediated anti-miR-129-5p silencing resulted in increased expression of HuD. Overall, these results support the conclusion that HuD expression is regulated by miR-129-5p. To further confirm their hypothesis, the inventors investigated HuD levels in early phase SOD1(G93A) murine spinal cord compared to wild-type murine spinal cord and they observed a significant downregulation in the first group (FIG. 4c, p<0.05). This shows that HuD in ALS mice is low.

Characterization of HuD-deficient mice indicates that this protein plays crucial roles in neuronal development, in particular controlling neuritogenesis (Akamatsu et al, 2005; DeBoer et al, 2014). To assess the effect of miR-129-5p on neuronal differentiation the inventors determined neurites outgrowth in SH-SY5Y/miR-129-1 and control cells treated with 10 μM RA. While control cells showed long branching processes, SH-SY5Y/miR-129-1 cells developed shorter, not properly formed neurite projections (FIG. 5a). The inventors also examined the expression of the neuronal markers NEUROD1, tubulin beta III (TUBB3) and MAP2, and of ASCL1, a marker of neuroblasts (Raposo et al, 2015). RT-qPCR analysis showed a significant decrease of all three neuronal markers, and an upregulation of ASCL1 in SH-SY5Y/miR-129-1 cells (FIG. 5b). In addition, the inventors measured the mRNA levels of three known HuD targets that function in neuronal differentiation (MUSASHI, MSI1 (Ratti et al, 2006)), and neurite extension GAP43) (Chung et al, 1997) and TAU/MAPT (Aranda-Abreu et al, 1999)) that are stabilized by HuD (Bronicki & Jasmin, 2013). Consistent with the idea that miR-129-5p inhibits neuronal differentiation through HuD targeting, the inventors found a significant downregulation of these three HuD-regulated transcripts (FIG. 5c). Finally, to verify that the impaired differentiation of SH-SY5Y/miR-129-1 cells was due to the miR129-mediated silencing of HuD expression, the inventors transiently transfected cells with a plasmid expressing the HuD ORF lacking the miR-129 binding site (FIG. 5d,e). As shown in FIG. 5f, SH-SY5Y/miR-129-1 expressing the exogenous miR-129-insensitive HuD mRNA restored HuD protein levels and displayed a robust neurite outgrowth in response to RA. In contrast, mock-transfected SH-SY5Y/miR-129-1 cells displayed undetectable levels of HuD protein and showed a rounder appearance with few, very short neurites. Taken together these results demonstrate that miR-129-5p regulates neurite formation by modulating HuD expression.

Example 3: MiR-129 Silencing Improves Neurological Phenotype and Survival in SOD1G93A Mice The inventors evaluated whether the inhibition of miRNA-129-5p had a significant effect also in vivo on the neuropathological phenotype of an ALS mouse model (SOD1G93A mice). Given its safety, efficacy and optimal translational profile we used the morpholino chemistry (MO) to synthesize a specific antisense oligonucleotide (ASO) to block the miR-129-5p precursor, miR-129-1. The inventors first tested the ability of MO to decrease miR-129 expression level, treating wild-type pups intracerobroventricularly (ICV) with 24 nmoles of MO and then harvested spinal cords after 1 week. RT-qPCR analysis showed a significant decrease of miR-129-5p expression levels after treatment (n=4/groups, p<0.01, FIG. 6a), demonstrating the efficacy of MO sequence. Accordingly, we also measured a significant (p<0.5) increase in HuD protein level in the same mice (FIG. 6b). These data show that morpholino treatment reduces miR129-5p level and rescues HuD level.

The inventors injected MO into SOD1G93A mice (MO-SOD1 mice) at early disease stage (Post-natal day 80) in their cerebrospinal fluid (CSF) by intracerebroventricular injection (Nizzardo et al., 2016). No major side effects were observed after treatment.

Remarkably, a significant increase in the lifespan of MO-SOD1 mice was observed. The median ages at death were 180 days for MO-SOD1 mice (n=14) and 160 days (n=12) for control-treated mice (ctr-SOD mice) ($\chi^{2=7.232}$, P=0.0072, Kaplan-Meier log-rank test) (FIG. 6c). The median survival of our SOD1(G93A) colony without any treatment is 153±6 days. MO-SOD1 mice showed an increased muscle strength compared to scr-SOD1 mice, as determined by significant improvement on the inverted grid assay at symptomatic disease stages (P=0.0048, FIG. 6d).

The disease is characterized by a progressive motor neuron (MN) degeneration. Thus, the inventors determined MN number through the histological analysis of spinal cord lumbar sections L1-L5, the most affected in SOD1G93A mice, at 120 days of age. MN loss was reduced after MO administration compared with scramble treatment (FIG. 6e), even if not statistically significant.

Neuromuscular junction (NMJ) denervation, axon degeneration and collateral sprouting for remaining MNs are ALS pathological hallmarks. The progressive MN cell loss associated with the retraction of axons from NMJs, that result denervated, are not sufficiently compensated by the axonal collateral sprouts from surviving MNs leading to progressive irreversible muscle paralysis. Interestingly, MO treatment significantly counteracts NMJ degeneration with a recovery of peripheral synapses; MO-SOD1 mice showed a significant increase of the number of fully innervated NMJs respect to scr-SOD1 mice (P<0.05, $\chi 2$=4.153) (FIG. 6f, g). In particular, the average of denervated NMJ is 74/100±7.39 for MO-SOD treated mice and 90/100±1.91 for ctr-SOD1-treated mice. The difference between the two means is statistically significant, p<0.05 (data not shown).

These data demonstrated the therapeutic efficacy of miR-129-1 silencing in ameliorating the murine ALS pathological phenotype, identifying the miR-129 pathway as a potential therapeutic target for ALS.

Overall, the present findings identify the miR-129/HuD pathway as a potential therapeutic target for ALS.

Discussion

In the present study, the inventors show that miR-129-5p is upregulated in different models of familial ALS and in sporadic ALS patient where it suppresses HuD expression, impairing neurite formation. Moreover, inhibition of miR-129-5p with an antagomir restors neuritogenesis in vitro and ameliorates survival and neuromuscular function when administered in the CSF of SOD1G93A mice in vivo.

Since their discovery, more than 2500 miRNAs have been identified in human cells according to the most recent release of the miRBase reference database (Kozomara & Griffiths-Jones, 2014). MiRNA pathways play a central role in multiple biological processes that are important in both normal and diseased states. Their function in disease has been particularly investigated in human cancers, and various miRNA-based therapeutics are currently being explored to modulated their expression (Shah & Calin, 2014). In the nervous system miRNAs are required for the survival of specific types of mature neurons in model organisms (De Pietri Tonelli et al, 2008). Moreover, the conditional ablation of Dicer, a crucial component of the miRNA processing machinery, in the mouse causes degeneration and death of various types of neurons (Damiani et al, 2008; Davis et al, 2008; De Pietri Tonelli et al, 2008; Haramati et al, 2010) supporting the idea that abnormal miRNA expression can contribute to the aetiology or the progression of neurodegenerative disorders.

In ALS, an involvement of miRNAs is supported by several intriguing observations. TDP-43 and FUS interact with components of the miRNA processing complexes affecting miRNA expression (Kawahara & Mieda-Sato, 2012; Kim et al, 2015) (Ballarino et al, 2013; Morlando et al, 2012). Importantly, DROSHA has been found in the cytoplasmic protein aggregates in postmortem brain samples of FTLD and ALS cases with C90RF72 mutations and TDP-43 pathology (Porta et al, 2015). Several studies have also reported altered miRNA expression in SOD1-linked ALS models (Marcuzzo et al, 2015; Marcuzzo et al, 2014) (Nolan et al, 2014), as well as in SOD1 fALS, and in sporadic ALS patients (Butovsky et al, 2015; Takahashi et al, 2015). However, no consistent changes have emerged so far. Rather it appears that the pool of dysregulated miRNAs may differ in the pre-symptomatic and in the symptomatic stages of the disease (Butovsky et al, 2012; De Felice et al, 2012), while a general downregulation of miRNAs has consistently been observed in postmortem spinal cord tissue of sporadic and familial ALS patients (Campos-Melo et al, 2013;

Figueroa-Romero et al, 2016) and in the late symptomatic SOD1(G93A) mice (Emde et al, 2015).

MiR-129-5p is highly expressed in human brain and spinal cord (FIG. 7, (Ludwig et al, 2016), and is particularly enriched in synaptosomal preparations (Zongaro et al, 2013). Despite these observations, very little is known about its function in the nervous system. The inventors identified by bioinformatic analysis and then validated experimentally the RNA-binding protein ELAVL4/HuD as a target of miR-129-5p. Indeed, the HuD protein was downregulated in human SH-SY5Y and in mouse NSC-34 cells overexpressing the miR-129 precursor. MiR-129-5p overexpression in SH-SY5Y and in NSC-34 cells inhibited the expression of neuronal differentiation markers and neurite outgrowth, a phenomenon that notably also occurred in cells overexpressing the mutant SOD1 protein, in which HuD is downregulated. The present results are particularly intriguing in the light of the loss of intraepidermal nerve fibers (the terminal endings of small-diameter sensory neurons located in dorsal root ganglia) that is observed in 75% of sporadic and familiar ALS patients (Dalla Bella et al, 2016; Weis et al, 2011) and in pre-symptomatic SOD1(G93A) mice (Sassone et al, 2016).

The present results show that HuD expression is reduced in cells and animals expressing the pathogenic SOD1G93A mutation and that administration of an antagomir of miR-129-5p rescues HuD expression in vitro and in vivo. HuD plays a fundamental role in controlling neuronal cell fate stimulating stimulates translation of mRNAs involved in neuronal cell commitment and axonogenesis(Tebaldi et al, 2018). HuD has been previously linked to neurodegeneration and to motor neuron function. In the hippocampus of Alzheimer's disease patients, a decrease in ELAVL proteins levels correlated with dementia progression (Amadio et al, 2009). Moreover, three separate studies have linked SNPs within the ELAVL4 locus to the development of Parkinson's Disease (DeStefano et al, 2008; Haugarvoll et al, 2007; Noureddine et al, 2005). The pivotal role of HuD in neuronal homeostasis is suggested also by the demonstration that prenatal knockout in mice disrupts the correct establishment and functioning of neocortical and hippocampal circuitry (DeBoer et al, 2014) and importantly motor neuron deficits (Akamatsu et al, 2005). HuD interacts with the SMN protein in the axonal compartments of neurons (Akten et al, 2011; Fallini et al, 2011; Hubers et al, 2011)(Hao et al, 2017) is essential for motor neuron development and function (Hao et al, 2017), and was reported to interact and be sequestered in TDP-43 inclusions in motor neuron cell bodies and neurites (Fallini et al, 2012).

Recently, De Santis et al. reported the upregulation and aggregation of HuD in FUS-linked ALS (De Santis R et al. 2019). Importantly, these authors observed that HuD is a common component of FUS-positive and TDP-43-positive neuronal cytoplasmic inclusions, in FUS and sporadic ALS patients (De Santis R et al. 2019). Since HuD sequestration in cytoplasmic inclusions may lead to a depletion of nuclear HuD or other types of HuD loss of function, the inventors hypothesize that HuD deficiency may be a common trait in ALS.

In the second part of the present invention the inventors show that CSF administration of MO against miR-129 precursor significantly ameliorated the ALS phenotype in a disease rodent model. The therapeutic effects of MO include statistically significant improvement of neuromuscular function, survival and protection of host MNs and NMJ innervation, as shown by neuropathological analyses. Interestingly, the therapeutic effect is more pronounced on NMJs innervation than on MN cell number increase suggesting that muscles in MO-SOD1 mice were reinnervated by terminal and collateral sprouts elongating from resistant MNs or/and that the spare NMJs were preserved. This specific effect can be correlated to the role of miR-129 target, HuD. Indeed, axonal regeneration regeneration following peripheral axon injury is associated with increased levels of HuD and of its direct target GAP43 (Anderson et al., 2003) and HuD has been shown to be able to restore axon outgrowth defects in SMA motor neurons (Akten et al., 2011). Further studies are needed to confirm this hypothesis. Moreover, the MO treatment was well-tolerated and no major side effects were observed. miR-129 effect may be also due to cells other than neurons (such as astrocytes or microglia). Previous in situ hybridization experiments on the rodent spinal cord suggest that miR-129, particularly miR-129-1, is predominantly expressed in both the cytoplasm and in the nucleus of the neuropil and large neuronal cells (Strickland et al. Neuroscience 2011). These in vivo results are of crucial importance for the development of a potential new therapeutic approach for ALS patients. Indeed, the recent approval of the ASO nursinen for SMA therapy (Wood et al, 2017), is a strong proof-of-principle that ASOs can be used to target the CNS for the treatment of neurological diseases. ASOs show widespread distribution in the brain and spinal cord after CSF administration using intraventricular or intrathecal injections. ASO delivery into the CSF by lumbar puncture has already been implemented in human clinical trials for ALS and other neurodegenerative diseases (Schoch & Miller, 2017). Importantly, the inventors obtained a significant positive impact with ASOs even if animals were treated after symptom onset, although still in the early symptomatic stages. This outcome is important given that human trials will likely be performed in the symptomatic patients.

The combined silencing of miR-129 and other miRNA, already studied in ALS, is an alternative therapeutic strategy, as their mechanisms of action are likely synergistic. For instance combination with miR-i55 may be used because of its function, mostly related to CNS inflammation through its ability to regulate microglia. Koval et al. demonstrated that widespread microRNA-155 inhibition with oligonucleotide-based miRNA inhibitors prolongs survival in ALS-model mice 9.5 days (7% increase) (Koval et al, 2013). Butovsky et al. confirmed this improvement after miRNA-i55 peripheral inhibition with locked nucleic acid (LNA) (11 days, 8% increase in survival, (Butovsky et al, 2015). Specifically, this group examined miRNA expression in the spinal cord microglia of SOD1 mice and in PBMCs of sALS patients, observing an increase in a subset of miRNAs that has been associated with inflammatory responses. Since the inventors demonstrated that miR-129 inhibition resulted in a higher survival extension of 20 days (12.5% increase), the combination of the two miRNA may increase therapeutic efficacy.

Overall the present data support miR129-5p and HuD as possible therapeutic targets in ALS and provides new insights in ALS pathology toward the development of novel meaningful therapeutic strategies for ALS.

REFERENCES

Akamatsu W, et al., (2005) *PNAS* 102: 4625-4630

Akten B, et al., (2011) *PNAS* 108: 10337-10342

Amadio M, et al., (2009) *Journal of Alzheimer's disease: JAD* 16: 409-419

Anderson K. D., et al., *Experimental neurology* 183, 100 (September, 2003)

Aranda-Abreu G E, et al., (1999) *The J. of neuroscience* 19: 6907-6917

Arosio A, et al., (2016) *Molecular and cellular neurosciences* 74: 10-17

Babetto E, et al., (2005) *Brain research Molecular brain research* 140: 63-72

Ballarino M, et al., (2013) *Oncogene* 32: 4646-4655

Benigni M, et al., (2016) *Neuromolecular medicine*

Bronicki L M, Jasmin B J (2013) *RNA (New York, NY)* 19: 1019-1037

Brooks B R, Miller R G, Swash M, Munsat T L (2000) *Amyotrophic lateral sclerosis and other motor neuron disorders: official publication of the World Federation of Neurology, Research Group on Motor Neuron Diseases* 1: 293-299

Buratti E, et al., (2010) *Febs J* 277: 2268-2281

Butovsky O, et al., (2015) *Annals of neurology* 77: 75-99

Butovsky O, et al., (2012) *The Journal of clinical investigation* 122: 3063-3087

Campos-Melo D, et al., (2013) *Molecular brain* 6: 26

Carri M T, et al., (1997) *FEBS letters* 414: 365-368

Chen L, et al., (2000) *Nature* 408: 936-943

Chia R, Chio A, Traynor B J (2018) *The Lancet Neurology* 17: 94-102

Chung S, et al., (1997) *The Journal of biological chemistry* 272: 6593-6598

Cloutier F, et al., (2015) *European journal of neurology* 23: 416-420

Dalla Bella E. et al., *European journal of neurology* 23, 416 (February, 2016).

Damiani D, et al., (2008) *J Neurosci* 28: 4878-4887

Davis T H, et al., (2008) *J Neurosci* 28: 4322-4330

De Felice B, et al., (2014) *Neurogenetics* 15: 243-253

De Felice B, et al., (2012) *Gene* 508: 35-40

De Pietri Tonelli D, et al., (2008). *Development* 135: 3911-3921

De Santis, R., et al. (2019). *Cell reports* 27, 3818 (Jun. 25, 2019)

DeBoer E M, et al., (2014) *The J. of neuroscience* 34: 3674-3686

DeJesus-Hernandez M, et al., (2011) *Neuron* 72: 245-256

DeStefano A L, et al. (2008) *Human genetics* 124: 95-99

Emde A, et al. (2015) *The EMBO journal* 34: 2633-2651

Fallini C, et al. (2012) *Human molecular genetics* 21: 3703-3718

Fallini C, et al. (2011) *The J. of neuroscience* 31: 3914-3925

Figueroa-Romero C, et al. (2016) *Molecular and cellular neurosciences* 71: 34-45

Freischmidt A, et al. (2015) *Neurobiology of aging* 36: 2660 e2615-2620

Galimberti D, et al. (2014) *Journal of Alzheimer's disease: JAD* 42: 1261-1267

Gaughwin P M, et al. (2011) *Human molecular genetics* 20: 2225-2237

Griffiths-Jones S, et al. *Nucleic acids research* 36, D154 (January, 2008).

Gurney M E, et al. (1994) *Science* 264: 1772-1775

Hao le T, et al. *J Neurosci*. 37, 11559 (Nov. 29, 2017)

Haramati S, et al. (2010) *PNAS* 107: 13111-13116

Haugarvoll K, et al. (2007) *Movement disorders* 22: 585-587

Huber W, et al. Bioinformatics 2002; 18 Suppl 1: 596-104.

Hubers L, et al. (2011) *Human molecular genetics* 20: 553-579

Jenny A, Minvielle-Sebastia L, Preker P J, and Keller W. Science 1996; 274: 1514-1517.

Kabashi E, et al., (2008) *Nature genetics* 40: 572-574

Kawahara Y, Mieda-Sato A (2012) *PNAS* 109: 3347-3352

37

Keller A, et al., (2011) *RNA biology* 8: 506-516

Kim K Y, et al., (2015) *Biochem. and biophysical research communications* 464: 236-243

Koval, E. D., et al., (2013). Human molecular genetics 22, 4127-4135

Kozomara A, Griffiths-Jones S (2014) *Nucleic acids research* 42: D68-73

Kwiatkowski T J, et al., (2009) *Science* 323: 1205-1208

Lee S T, et al., (2012) *Annals of neurology* 72: 269-277

Lenzken S C, et al. (2011) *Hum Mutat* 32: 168-182

Lestanova, Z., Bacova, Z., Kiss, A. et al. *J Mol Neurosci* 59, 184-192 (2016)

Liang C, et al. (2012) *Brain research* 1455: 103-113

Loffreda A, et al. (2015) *Biomolecules* 5: 2363-2387

Ludwig N, et al. (2016) *Nucleic acids research* 44: 3865-3877

Majounie E, et al. (2012) *The Lancet Neurology* 11: 323-330

Marcuzzo S, et al. (2015) *Molecular brain* 8: 5

Marcuzzo S, et al. (2014) *Experimental neurology* 253: 91-101

McKhann G, et al., (1984) *Neurology* 34:939-944

Miyachi M, et al. (2010) *Biochemical and biophysical research communications* 400: 89-93

Morlando M, et al. (2012) *The EMBO journal* 31: 4502-4510

Nizzardo M et al., *Scientific reports* 6, 21301 (Feb. 16, 2016).

Nolan K, et al. (2014) *Journal of molecular neuroscience: MN* 53: 231-241

Noureddine M A, et al., (2005) *Human genetics* 117: 27-33

Packer A N, et al., (2008) *The J. of neuroscience* 28: 14341-14346

Parisi C, et al., (2016) *Cell death and differentiation* 23: 531-541

Porta S, et al., (2015) *Journal of neuropathology and experimental neurology* 74: 380-387

Prell T, et al., (2012) *The European journal of neuroscience* 35: 652-660

Raposo A A, et al., (2015) *Cell reports*

Ratti A, et al., (2006) *Journal of cell science* 119: 1442-1452

Renton A E, Chio A, Traynor B J (2014) *Nature neuroscience* 17: 17-23

38

Reber S, et al. EMBO J 2016; 35: 1504-1521.

Robinson M D, et al., (2010) *Bioinformatics* (Oxford, England) 26: 139-140

Rosen D R, et al. (1993) *Nature* 362: 59-62

Rumble S M, et al., (2009) *PLoS computational biology* 5: e1000386

Sala G, et al., (2010) *J Neural Transm* 117: 1093-1098

Sassone J, et al., (2016) *Human molecular genetics* 25: 1588-1599

Schaefer A, et al., (2007) *The Journal of experimental medicine* 204: 1553-1558

Schneider C A, Rasband W S, Eliceiri K W (2012) *Nature methods* 9: 671-675

Schoch K M, Miller T M (2017) *Neuron* 94: 1056-1070

Shah M Y, Calin G A (2014) *Wiley interdisciplinary reviews RNA* 5: 537-548

Sreedharan J, et al., (2008) *Science* (New York, NY) 319: 1668-1672

Strickland, E. R., et al., *Neuroscience* 186, 146 (Jun. 14, 2011)

Sun A X, Crabtree G R, Yoo A S (2013) *Current opinion in cell biology* 25: 215-221

Takahashi I, et al., (2015) *Molecular brain* 8: 67

Tasca E, Pegoraro V, Merico A, Angelini C (2016) *Clinical neuropathology* 35: 22-30

Tebaldi T, et al., (2018) *Molecular cell* 71: 256-270 e210

Tremolizzo L, et al., (2013) *Amyotrophic lateral sclerosis & frontotemporal degeneration* 14: 157-158

Vance C, et al., (2009) *Science* (New York, NY) 323: 1208-1211

Volinia S, et al., (2010) *Bioinformatics* (Oxford, England) 26: 91-97

Weis J, et al., (2011) *Neurology* 76: 2024-2029

Williams A H, et al., (2009) *Science* (New York, NY) 326: 1549-1554

Wood M J A, Talbot K, Bowerman M (2017) *Human molecular genetics* 26: R151-R159

Wu Y, Wang G, Scott S A, Capecchi M R (2008) *Development* 135: 171-182

Yokoseki A, et al., (2008) *Annals of neurology* 63: 538-542

Zongaro S, et al., (2013) *Human molecular genetics* 22: 1971-1982

The invention claimed is:

1. A method for treating amyotrophic lateral sclerosis comprising administering a morpholino antisense oligonucleotide inhibitor of miR-129 to a subject diagnosed with amyotrophic lateral sclerosis, wherein said morpholino antisense oligonucleotide inhibitor of miR-129 comprises the sequence of SEQ ID NO: 3.

2. The method according to claim 1, wherein said morpholino antisense oligonucleotide inhibitor of miR-129 is:
    a single-stranded or double-stranded nucleic acid molecule, an siRNA molecule, an antisense oligonucleotide, derivatives and mixtures thereof.

3. The method of claim 1, wherein the morpholino antisense oligonucleotide inhibitor of miR-129 is administered to the subject intracerebroventricularly, orally, rectally, transmucosal, intestinally, enterally, through inhalation, intraventricularly, intraperitoneally, intranasally, or parenterally.

4. The method of claim 1, wherein the subject has SOD1-associated ALS.

5. The method of claim 1, wherein said morpholino antisense oligonucleotide inhibitor of miR-129 consists the sequence of SEQ ID NO: 3.

* * * * *

SEQUENCE LISTING

```
<160> NUMBER OF SEQ ID NOS: 42

<210> SEQ ID NO 1
<211> LENGTH: 72
<212> TYPE: DNA
<213> ORGANISM: Artificial Sequence
<220> FEATURE:
<223> OTHER INFORMATION: synthetic

<400> SEQUENCE: 1
ggaucuuuuu gcggucuggg cuugcuguuc cucucaacag uagucaggaa gcccuuaccc      60
caaaaaguau cu                                                          72

<210> SEQ ID NO 2
<211> LENGTH: 21
<212> TYPE: DNA
<213> ORGANISM: Artificial Sequence
<220> FEATURE:
<223> OTHER INFORMATION: synthetic

<400> SEQUENCE: 2
```

-continued cuuuuugcgg ucugggcuug c                                                    21

<210> SEQ ID NO 3
<211> LENGTH: 25
<212> TYPE: DNA
<213> ORGANISM: Artificial Sequence
<220> FEATURE:
<223> OTHER INFORMATION: synthetic

<400> SEQUENCE: 3
acagcaagcc cagaccgcaa aaaga                                                25

<210> SEQ ID NO 4
<211> LENGTH: 19
<212> TYPE: DNA
<213> ORGANISM: Artificial Sequence
<220> FEATURE:
<223> OTHER INFORMATION: synthetic

<400> SEQUENCE: 4
acatcctcga ctggaagaa                                                       19

<210> SEQ ID NO 5
<211> LENGTH: 24
<212> TYPE: DNA
<213> ORGANISM: Artificial Sequence
<220> FEATURE:
<223> OTHER INFORMATION: synthetic

<400> SEQUENCE: 5
tgtaaacatc ctacactcag ctaa                                                 24

<210> SEQ ID NO 6
<211> LENGTH: 25
<212> TYPE: DNA
<213> ORGANISM: Artificial Sequence
<220> FEATURE:
<223> OTHER INFORMATION: synthetic

<400> SEQUENCE: 6
tgtaaacatc ctacactctc agcaa                                                25

<210> SEQ ID NO 7
<211> LENGTH: 18
<212> TYPE: DNA
<213> ORGANISM: Artificial Sequence
<220> FEATURE:
<223> OTHER INFORMATION: synthetic

<400> SEQUENCE: 7
catccccgac tggaagaa                                                        18

<210> SEQ ID NO 8
<211> LENGTH: 20
<212> TYPE: DNA
<213> ORGANISM: Artificial Sequence
<220> FEATURE:
<223> OTHER INFORMATION: synthetic

<400> SEQUENCE: 8
aacatccttg actggaagaa                                                      20

<210> SEQ ID NO 9
<211> LENGTH: 20
<212> TYPE: DNA
<213> ORGANISM: Artificial Sequence -continued

```
<220> FEATURE:
<223> OTHER INFORMATION: synthetic

<400> SEQUENCE: 9
caccatctga aatcggttaa                                                    20

<210> SEQ ID NO 10
<211> LENGTH: 25
<212> TYPE: DNA
<213> ORGANISM: Artificial Sequence
<220> FEATURE:
<223> OTHER INFORMATION: synthetic

<400> SEQUENCE: 10
tagcaccatt tgaaatcagt gttaa                                              25

<210> SEQ ID NO 11
<211> LENGTH: 24
<212> TYPE: DNA
<213> ORGANISM: Artificial Sequence
<220> FEATURE:
<223> OTHER INFORMATION: synthetic

<400> SEQUENCE: 11
tggaatgtaa agaagtatgt ataa                                               24

<210> SEQ ID NO 12
<211> LENGTH: 24
<212> TYPE: DNA
<213> ORGANISM: Artificial Sequence
<220> FEATURE:
<223> OTHER INFORMATION: synthetic

<400> SEQUENCE: 12
tggaatctaa ggaagtgtgt ggaa                                               24

<210> SEQ ID NO 13
<211> LENGTH: 23
<212> TYPE: DNA
<213> ORGANISM: Artificial Sequence
<220> FEATURE:
<223> OTHER INFORMATION: synthetic

<400> SEQUENCE: 13
gcagcacata atggtttgtg aaa                                                23

<210> SEQ ID NO 14
<211> LENGTH: 22
<212> TYPE: DNA
<213> ORGANISM: Artificial Sequence
<220> FEATURE:
<223> OTHER INFORMATION: synthetic

<400> SEQUENCE: 14
gcagcacatc atggtttaca aa                                                 22

<210> SEQ ID NO 15
<211> LENGTH: 21
<212> TYPE: DNA
<213> ORGANISM: Artificial Sequence
<220> FEATURE:
<223> OTHER INFORMATION: synthetic

<400> SEQUENCE: 15
cagcacgtaa atattggcga a                                                  21
```

-continued

```
<210> SEQ ID NO 16
<211> LENGTH: 23
<212> TYPE: DNA
<213> ORGANISM: Artificial Sequence
<220> FEATURE:
<223> OTHER INFORMATION: synthetic

<400> SEQUENCE: 16
tagcagcaca gaaatattgg caa                                            23

<210> SEQ ID NO 17
<211> LENGTH: 25
<212> TYPE: DNA
<213> ORGANISM: Artificial Sequence
<220> FEATURE:
<223> OTHER INFORMATION: synthetic

<400> SEQUENCE: 17
gtgaaatgtt taggaccact agaaa                                          25

<210> SEQ ID NO 18
<211> LENGTH: 25
<212> TYPE: DNA
<213> ORGANISM: Artificial Sequence
<220> FEATURE:
<223> OTHER INFORMATION: synthetic

<400> SEQUENCE: 18
tctttggtta tctagctgta tgaaa                                          25

<210> SEQ ID NO 19
<211> LENGTH: 23
<212> TYPE: DNA
<213> ORGANISM: Artificial Sequence
<220> FEATURE:
<223> OTHER INFORMATION: synthetic

<400> SEQUENCE: 19
gcagtccatg ggcatattca caa                                            23

<210> SEQ ID NO 20
<211> LENGTH: 18
<212> TYPE: DNA
<213> ORGANISM: Artificial Sequence
<220> FEATURE:
<223> OTHER INFORMATION: synthetic

<400> SEQUENCE: 20
cacgcggtga atgccaaa                                                  18

<210> SEQ ID NO 21
<211> LENGTH: 21
<212> TYPE: DNA
<213> ORGANISM: Artificial Sequence
<220> FEATURE:
<223> OTHER INFORMATION: synthetic

<400> SEQUENCE: 21
gtgaggttct tgggagccaa a                                              21

<210> SEQ ID NO 22
<211> LENGTH: 23
<212> TYPE: DNA
<213> ORGANISM: Artificial Sequence
<220> FEATURE:
<223> OTHER INFORMATION: synthetic
```

<400> SEQUENCE: 22
ctgagaccct ttaacctgtg aaa                                  23

<210> SEQ ID NO 23
<211> LENGTH: 23
<212> TYPE: DNA
<213> ORGANISM: Artificial Sequence
<220> FEATURE:
<223> OTHER INFORMATION: synthetic

<400> SEQUENCE: 23
ccctgagacc ctaacttgtg aaa                                  23

<210> SEQ ID NO 24
<211> LENGTH: 22
<212> TYPE: DNA
<213> ORGANISM: Artificial Sequence
<220> FEATURE:
<223> OTHER INFORMATION: synthetic

<400> SEQUENCE: 24
cagtctacag ccatggtcga aa                                   22

<210> SEQ ID NO 25
<211> LENGTH: 20
<212> TYPE: DNA
<213> ORGANISM: Artificial Sequence
<220> FEATURE:
<223> OTHER INFORMATION: synthetic

<400> SEQUENCE: 25
gtgcttacag tgcaggtaga                                     20

<210> SEQ ID NO 26
<211> LENGTH: 26
<212> TYPE: DNA
<213> ORGANISM: Artificial Sequence
<220> FEATURE:
<223> OTHER INFORMATION: synthetic

<400> SEQUENCE: 26
tggaagacta gtgattttgt tgtaaa                               26

<210> SEQ ID NO 27
<211> LENGTH: 26
<212> TYPE: DNA
<213> ORGANISM: Artificial Sequence
<220> FEATURE:
<223> OTHER INFORMATION: synthetic

<400> SEQUENCE: 27
taatactgcc gggtaatgat ggaaaa                               26

<210> SEQ ID NO 28
<211> LENGTH: 24
<212> TYPE: DNA
<213> ORGANISM: Artificial Sequence
<220> FEATURE:
<223> OTHER INFORMATION: synthetic

<400> SEQUENCE: 28
aggcagcggg gtgtagtgga taaa                                 24

<210> SEQ ID NO 29

```
<211> LENGTH: 24
<212> TYPE: DNA
<213> ORGANISM: Artificial Sequence
<220> FEATURE:
<223> OTHER INFORMATION: synthetic

<400> SEQUENCE: 29
tatgtccttt ggactacatc gaaa                                              24

<210> SEQ ID NO 30
<211> LENGTH: 24
<212> TYPE: DNA
<213> ORGANISM: Artificial Sequence
<220> FEATURE:
<223> OTHER INFORMATION: synthetic

<400> SEQUENCE: 30
aagcattctt tcattggttg gaaa                                              24

<210> SEQ ID NO 31
<211> LENGTH: 22
<212> TYPE: DNA
<213> ORGANISM: Artificial Sequence
<220> FEATURE:
<223> OTHER INFORMATION: synthetic

<400> SEQUENCE: 31
tggatcagtg gttcgagtca aa                                                22

<210> SEQ ID NO 32
<211> LENGTH: 24
<212> TYPE: DNA
<213> ORGANISM: Artificial Sequence
<220> FEATURE:
<223> OTHER INFORMATION: synthetic

<400> SEQUENCE: 32
gatgaggacc ttttcacaga cctg                                              24

<210> SEQ ID NO 33
<211> LENGTH: 20
<212> TYPE: DNA
<213> ORGANISM: Artificial Sequence
<220> FEATURE:
<223> OTHER INFORMATION: synthetic

<400> SEQUENCE: 33
tccactccaa cacagccaac                                                   20

<210> SEQ ID NO 34
<211> LENGTH: 32
<212> TYPE: DNA
<213> ORGANISM: Artificial Sequence
<220> FEATURE:
<223> OTHER INFORMATION: synthetic

<400> SEQUENCE: 34
cttacgcgtt tgttttcttc ttccctcgtt ta                                     32

<210> SEQ ID NO 35
<211> LENGTH: 24
<212> TYPE: DNA
<213> ORGANISM: Artificial Sequence
<220> FEATURE:
<223> OTHER INFORMATION: synthetic

<400> SEQUENCE: 35
```

-continued

```
ccaaacaaag cccacaagtc ctga                                            24

<210> SEQ ID NO 36
<211> LENGTH: 29
<212> TYPE: DNA
<213> ORGANISM: Artificial Sequence
<220> FEATURE:
<223> OTHER INFORMATION: synthetic

<400> SEQUENCE: 36
attacgcgta tgtcatcagg tatccccct                                       29

<210> SEQ ID NO 37
<211> LENGTH: 16
<212> TYPE: DNA
<213> ORGANISM: Artificial Sequence
<220> FEATURE:
<223> OTHER INFORMATION: synthetic

<400> SEQUENCE: 37
tcttttgcgt cgccag                                                     16

<210> SEQ ID NO 38
<211> LENGTH: 22
<212> TYPE: DNA
<213> ORGANISM: Artificial Sequence
<220> FEATURE:
<223> OTHER INFORMATION: synthetic

<400> SEQUENCE: 38
cccgttctca gccttgacgg tg                                              22

<210> SEQ ID NO 39
<211> LENGTH: 25
<212> TYPE: DNA
<213> ORGANISM: Artificial Sequence
<220> FEATURE:
<223> OTHER INFORMATION: synthetic

<400> SEQUENCE: 39
cctcttacct cagttacaat ttata                                           25

<210> SEQ ID NO 40
<211> LENGTH: 21
<212> TYPE: DNA
<213> ORGANISM: Artificial Sequence
<220> FEATURE:
<223> OTHER INFORMATION: synthetic

<400> SEQUENCE: 40
agaaaaaaaa aaaacaaaaa a                                               21

<210> SEQ ID NO 41
<211> LENGTH: 21
<212> TYPE: DNA
<213> ORGANISM: Artificial Sequence
<220> FEATURE:
<223> OTHER INFORMATION: synthetic

<400> SEQUENCE: 41
cguucggguc uggcguuuuu c                                               21

<210> SEQ ID NO 42
<211> LENGTH: 21
<212> TYPE: DNA
```

-continued

```
<213> ORGANISM: artificial
<220> FEATURE:
<223> OTHER INFORMATION: synthetic

<400> SEQUENCE: 42
agaaaaaaaa aaaacattta a                                            21
```